United States Patent
Hosseinzadeh et al.

(10) Patent No.: US 11,524,979 B2
(45) Date of Patent: Dec. 13, 2022

(54) MACROCYCLIC POLYPEPTIDES

(71) Applicant: UNIVERSITY OF WASHINGTON, Seattle, WA (US)

(72) Inventors: Parisa Hosseinzadeh, Seattle, WA (US); David Baker, Seattle, WA (US); Gaurav Bhardwaj, Seattle, WA (US); Vikram K. Mulligan, Seattle, WA (US)

(73) Assignee: University of Washington, Seattle, WA (US)

( * ) Notice: Subject to any disclaimer, the term of this patent is extended or adjusted under 35 U.S.C. 154(b) by 47 days.

(21) Appl. No.: 16/610,574

(22) PCT Filed: Jun. 14, 2018

(86) PCT No.: PCT/US2018/037452
§ 371 (c)(1),
(2) Date: Nov. 4, 2019

(87) PCT Pub. No.: WO2018/232062
PCT Pub. Date: Dec. 20, 2018

(65) Prior Publication Data
US 2020/0223890 A1    Jul. 16, 2020

Related U.S. Application Data

(60) Provisional application No. 62/581,257, filed on Nov. 3, 2017, provisional application No. 62/520,011, filed on Jun. 15, 2017.

(51) Int. Cl.
*C07K 7/64* (2006.01)

(52) U.S. Cl.
CPC ........................... *C07K 7/64* (2013.01)

(58) Field of Classification Search
None
See application file for complete search history.

(56) References Cited

U.S. PATENT DOCUMENTS

| | | | |
|---|---|---|---|
| 8,022,252 B2 | 9/2011 | Deslongchamps et al. | |
| 8,808,694 B2 | 8/2014 | Nash et al. | |
| 2009/0324707 A1* | 12/2009 | Pluschke | C07K 7/56 424/450 |
| 2012/0258126 A1* | 10/2012 | Scholler | A61K 39/00 424/186.1 |
| 2014/0322240 A1* | 10/2014 | Rowe | A61K 39/015 530/389.1 |
| 2016/0175386 A1* | 6/2016 | Mapelli | A61P 31/16 514/1.4 |
| 2017/0037084 A1 | 2/2017 | Fasan | |

FOREIGN PATENT DOCUMENTS

WO    WO 2001/097098    12/2001

OTHER PUBLICATIONS

Tugyi et al. (Proc Natl Acad Sci USA. Jan. 11, 2005;102(2):413-8) (Year: 2005).*
Joo et al. (Biomol Ther 20(1), 19-26 (2012)) (Year: 2012).*
The International Search Report (ISR) with Written Opinion for PCT/US201837452 dated Oct. 29, 2018, pp. 1-11.
Thapa et al., "The Emergence of Cyclic Peptides: The Potential of Bioengineered Peptide Drugs," Int. J. Pept. Res. Ther. 20:545-51 (2014).
International Search Report of the International Searching Authority for International Application No. PCT/US2018/37452; dated Oct. 29, 2018, pp. 1-5.
Abraham et al., "GROMACS: High Performance Molecular Simulations through Multi-Level Parallelism from Laptops to Supercomputers," SoftwareX 1-2:19-25 (2015).
Alford et al.,"The Rosetta All-Atom Energy Function for Macromolecular Modeling and Design," J. Chem. Theory Comput. 13:3031-48 (2017).
Berendsen et al., "Molecular dynamics with coupling to an external bath," J. Chem. Phys. 81:3684-90 (1984).
Bhardwaj et al., "Accurate de novo design of hyperstable constrained peptides," Nature 538:329-35 (2016).
Boyken et al., "De novo design of protein homo-oligomers with modular hydrogen-bond network-mediated specificity," Science 352:680-87 (2016).
Bradley et al., "Toward high-resolution de novo structure prediction for small proteins," Science 309:1868-71 (2005).
Bussi et al., "Canonical sampling through velocity rescaling," J Chem. Phys. 126:014101 (8 pages) (2007).
Coutsias et al., "A kinematic view of loop closure," J. Comput. Chem. 25:510-28 (2004).
Coutsias et al., "Using quaternions to calculate RMSD," J. Comput Chem 25:1849-57 (2004).
Craik et al., "The future of peptide-based drugs," Chem. Biol. Drug Des. 81:136-47 (2013).
Cronkite-Ratcliff et al., "MSMExplorer: visualizing Markov state models for biomolecule folding simulations," Bioinformatics 29:950-52 (2013).
Delaglio et al., "NMRPipe: a multidimensional spectral processing system based on UNIX pipes," J. Biomol. NMR. 6:277-93 (1995).
Deng et al., "Ultra-High Resolution Ion Mobility Separations Utilizing Traveling Waves in a 13 m Serpentine Path Length Structures for Lossless Ion Manipulations Module," Anal. Chem. 88:8957-64 (2016).
Driggers et al., "The exploration of macrocycles for drug discovery—an underexploited structural class," Nat. Rev. Drug Discov. 7:608-24 (2008).
Essmann et al., "A smooth particle mesh Ewald method," J. Chem. Phys. 103:8577-93 (1995).
Fleishman et al., "RosettaScripts: a scripting language interface to the Rosetta macromolecular modeling suite," PLoS One 6:e20161 (2011).

(Continued)

*Primary Examiner* — Sergio Coffa
(74) *Attorney, Agent, or Firm* — McDonnell Boehnen Hulbert & Berghoff

(57) ABSTRACT

Disclosed herein are macrocyclic polypeptides having no more than 3 amino acid substitutions compared to the amino acid sequence of any one of SEQ ID NO: 1-2.37 or a mirror image thereof, wherein the polypeptide includes both L and D amino acids, libraries of such polypeptides, and uses thereof.

10 Claims, 2 Drawing Sheets

Specification includes a Sequence Listing.

(56) References Cited

OTHER PUBLICATIONS

Fosgerau et al., "Peptide therapeutics: current status and future directions," Drug Discov. Today. 20:122-28 (2015).
Gallant et al.,"Synthesis, Structure, and Computational Studies of Soluble Conjugated Multidentate Macrocycles," J. Org Chemistry 70(20):7936-46 (2005).
Gavenonis et al., "Comprehensive analysis of loops at protein-protein interfaces for macrocycle design," Nature Chemical Biology 10:716-22 (2014).
Gray et al., "Protein-protein docking with simultaneous optimization of rigid-body displacement and side-chain conformations," J. Mol. Biol. 331:281-99 (2003).
Gray et al., "Combinatorial peptide libraries: mining for cell-binding peptides," Chem. Rev. 114:1020-81 (2014).
Hess et al., "LINCS: A linear constraint solver for molecular simulations," J. Comput. Chem. 18:1463-72 (1997).
Huang et al., "De novo design of a four-fold symmetric TIM-barrel protein with atomic-level accuracy," Nat. Chem. Biol. 12:29-34 (2015).
Huang et al., "High thermodynamic stability of parametrically designed helical bundles," Science 346:481-85 (2014).
Huang et al., "The coming of age of de novo protein design," Nature 537:320-27 (2016).
Hutchinson et al., "A revised set of potentials for β-turn formation in proteins," Protein Sci. 3:2207-16 (1994).
Ibrahim et al., "Ion funnel trap interface for orthogonal time-of-flight mass spectrometry," Anal. Chem. 79:7845-52 (2007).
Ibrahim et al., "New frontiers for mass spectrometry based upon structures for lossless ion manipulations," Analyst 142:1010-21 (2017).
Khatib et al., "Algorithm discovery by protein folding game players," Proc. Natl.Proc. Natl. Acad. Sci. U. S. A. 108:18949-53 (2011).
Lange et al., "Recognition dynamics up to microseconds revealed from an RDC-derived ubiquitin ensemble in solution," Science 320:1471-75 (2008).
Li et al., "Calibur: a tool for clustering large number of protein decoys," BMC Bioinformatics 11:25 (2010).
Lindorff-Larsen et al., "Improved Side-Chain Torsion Potentials for the Amber ff99SB Protein Force Field," Proteins 78(8):1950-58 (2010).
Liu et al., "Tumor-targeting peptides from combinatorial libraries," Adv. Drug Deliv. Rev. 110-111:13-37 (2017).
Mandell et al., "Sub-angstrom accuracy in protein loop reconstruction by robotics-inspired conformational sampling," Nat. Methods. 6:551-52 (2009).
Marasco et al., "Past and future perspectives of synthetic peptide libraries." Curr. Protein Pept. Sci. 9:447-67 (2008).
Marcos et al., "Principles for designing proteins with cavities formed by curved β sheets," Science 355:201-06 (2017).
Naritomi et al., "Slow dynamics in protein fluctuations revealed by time-structure based independent component analysis: the case of domain motions," J. Chem. Phys. 134:065101 (2011).
Nielsen et al., "Orally Absorbed Cyclic Peptides," Chem. Rev. 117:8094-8128 (2017).
North et al., "A new clustering of antibody CDR loop conformations" J. Mol. Biol. 406:228-56 (2011).
Obexer et al., "Exploring sequence space: harnessing chemical and biological diversity towards new peptide leads," Curr. Opin. Chem. Biol. 38:52-61 (2017).
Páll et al., "A flexible algorithm for calculating pair interactions on SIMD architectures," Comput. Phys. Commun. 184:2641-50 (2013).
Páll et al., "Tackling Exascale Software Challenges in Molecular Dynamics Simulations with GROMACS," Solving Software Challenges for Exascale, 3-27. Springer, Cham (2014).
Park et al., "Simultaneous Optimization of Biomolecular Energy Functions on Features from Small Molecules and Macromolecules," J. Chem. Theory Comput. 12:6201-12 (2016).
Passioura & Suga "A RaPID way to discover nonstandard macrocyclic peptide modulators of drug targets," Chem. Commun. 53:1931-40 (2017).
Pérez-Herández et al., "Identification of slow molecular order parameters for Markov model construction," J. Chem. Phys. 139:015102 (2013).
Rizo et al., "Constrained Peptides: Models of Bioactive Peptides and Protein Substructures," Annu. Rev. Biochem. 61:387-416(1992).
Schwantes et al., "Improvements in Markov State Model Construction Reveal Many Non-Native Interactions in the Folding of NTL9," J. Chem. Theory Comput. 9: 2000-2009 (2013).
Schwieters et al., "The Xplor-NIH NMR molecular structure determination package," J. Magn. Reson. 160:65-73 (2003).
Schwieters et al., "Using Xplor—NIH for NMR molecular structure determination," Prog. Nucl. Magn. Reson. Spectrosc. 48:47-62 (2006).
Singh et al., "Conformationally based design of macrocycles as antitumor agents," Current opinion in drug discovery & development 11(4):544-52 (2008).

* cited by examiner

MACROCYCLIC POLYPEPTIDES

CROSS REFERENCE

This application is a U.S. national phase of International Application No. PCT/US2018/037452, filed on Jun. 14, 2018, which claims priority to U.S. Provisional Application No. 62/520,011, filed Jun. 15, 2017; and U.S. Provisional Application No. 62/581,257, filed Nov. 3, 2017, all of which are incorporated by reference herein in their entirety.

BACKGROUND

The high stability, diverse functionality, and favorable pharmacokinetic properties of macrocyclic peptides make them promising starting points for targeted therapeutics. However, there are few well-characterized natural macrocycles and they are difficult to repurpose for new functions. Thus most current approaches focus on random library selection methods, which, while powerful, only cover a small fraction of the vast sequence space that can be accessed by even short sequences of L- and D-amino acids, and often yield peptides which are not structured in the absence of target. Methods are needed for designing ordered macrocycles with shapes precisely crafted to bind their targets and with functionalities common in medicinal chemistry, but absent in the natural 20 amino acids, positioned at critical interaction sites.

SUMMARY

In one aspect are provided macrocyclic polypeptides comprising or consisting of a polypeptide having no more than 3 amino acid substitutions compared to the amino acid sequence of any one of SEQ ID NO: 1-237 or a mirror image thereof, wherein the polypeptide includes both L and D amino acids. In one embodiment, the polypeptides have at least one proline residue. In another embodiment, the polypeptides are between 7 and 14 amino acid residues in length, or between 7 and 10 amino acid residues in length. In a further embodiment, each amino acid substitution occurs at a non-proline position. In one embodiment, the amino acid substitutions do not include any non-proline residues being substituted with proline. In another embodiment, each amino acid substitution maintains the chirality of the amino acid replaced. In a further embodiment, each amino acid substitution is an alpha amino acid. In one embodiment, the polypeptides have at least 2, 3, 4, 5, 6, 7, 8, or more D amino acid residues. In another embodiment, the polypeptides have no more than 1 or 2 amino acid substitutions compared to the amino acid sequence of any one of SEQ ID NO: 1-237 or a mirror image thereof. In a further embodiment, the polypeptides comprise or consist of the amino acid sequence of any one of SEQ ID NO: 1-237 or a mirror image thereof.

In a further aspect the disclosure provides polypeptide libraries, comprising two or more polypeptides according to any embodiment or combination of embodiments of the disclosure.

In another aspect the disclosure provides for use of the polypeptides or the polypeptide libraries of any embodiment or combination of embodiments of the disclosure as a scaffold for target-based drug design or to screen molecules of interest for binding to one or more of the polypeptides.

DETAILED DESCRIPTION

Figure 1:
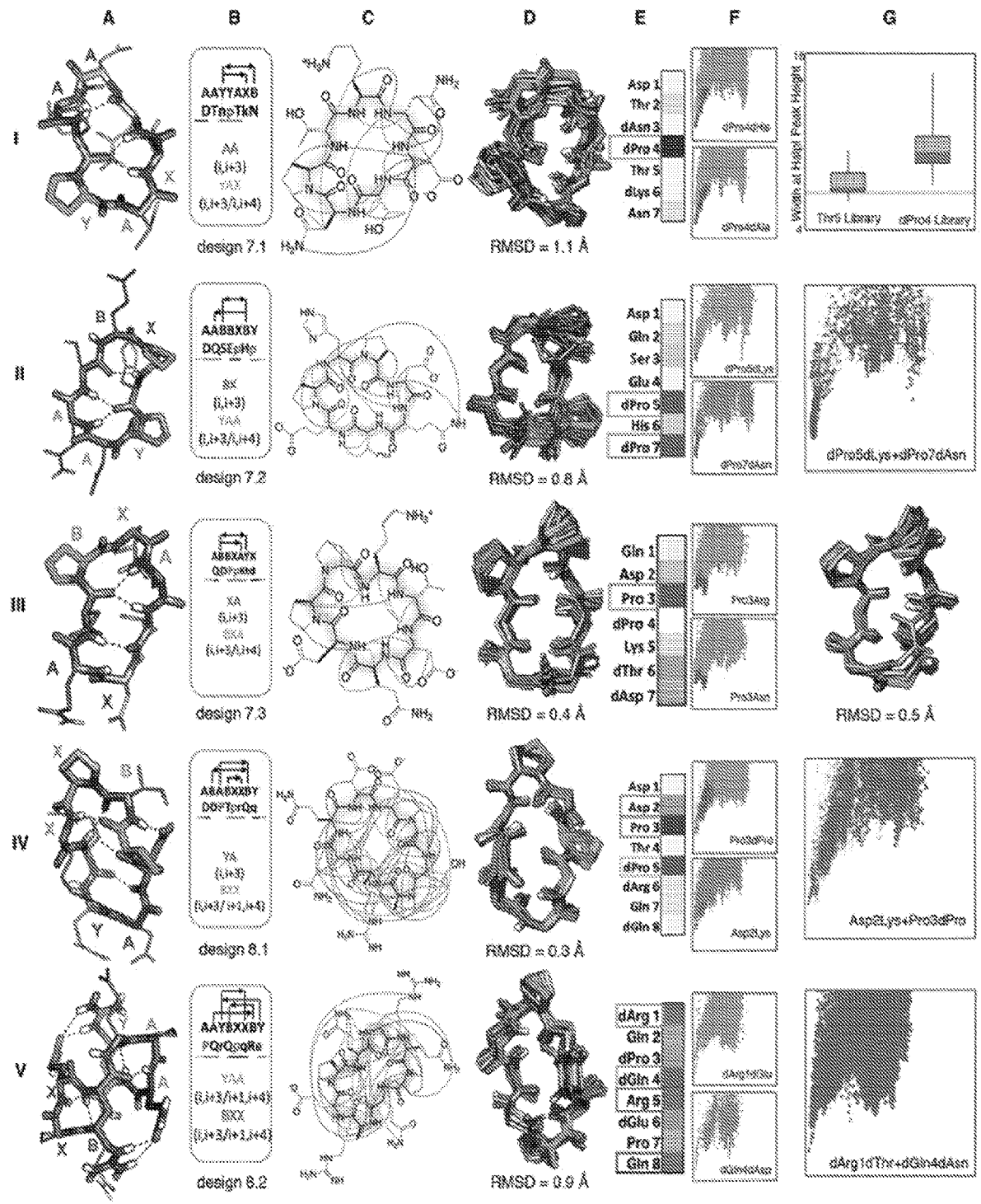
FIG. 1. 7-8 residue macrocycle NMR structures are very close to design models. Columns A: Design model, B: amino acid sequence, torsion bin string, hydrogen bond pattern and building block composition, C: observed backbone-backbone, backbone-sidechain) and sidechain-sidechain NOEs, D: overlay of design model on MD refined NMR ensemble (the average backbone rmsd to the NMR ensemble is indicated) for the design indicated at the bottom of column B. E: Average decrease in the propensity to favor the designed state ($P_{Near}$, see methods) over all mutations at each position. Darker gray indicates larger decreases; positions particularly sensitive to mutation are boxed and indicated by color in the design model in column a. F: representative energy funnels for mutations at key positions as compared to the design sequence. Row I, column G: experimental SLIM data. Distribution of peak width at half height for peptide libraries with all amino substitutions at positions 4 and 5; the position 4 library has a broader distribution consistent with the computed energy landscape in column F. Rows II, IV, V, column G: Representative energy landscapes for double substitutions of critical residues overlaid on the original design landscape. Row III, column G: overlay of design model on alternative structure NMR ensemble (turn flip at bottom right).

All references cited are herein incorporated by reference in their entirety.

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Amino acid residues in D-form are noted with a "D" preceding the amino acid residue abbreviation. Amino acid residues in L-form are noted with just the amino acid residue abbreviation, noting that Glycine is non-chiral.

All embodiments of any aspect of the invention can be used in combination, unless the context clearly dictates otherwise.

In one aspect, the disclosure provides non-naturally occurring macrocyclic polypeptide comprising or consisting of a polypeptide having no more than 3 amino acid substitutions compared to the amino acid sequence of any one of SEQ ID NO: 1-237 or a mirror image thereof, wherein the polypeptide includes both L and D amino acids.

As shown in the examples that follow, the inventors have enumerated the stable structures that can be adopted by macrocyclic peptides composed of L- and D-amino acids by near exhaustive backbone sampling followed by sequence design and energy landscape calculations, and have identified 237 designs (SEQ ID NOS:1-237) predicted to fold into single stable structures, many times more than the number of currently available unbound peptide macrocycle structures. The polypeptides of the disclosure are attractive starting points for developing new therapeutics. One approach to inhibitor design is scaffolding loops at binding interfaces in the PDB; such scaffolding can increase binding affinity by pre-organizing the loops in the binding-competent conformation, enable additional interactions with the target, and improve cell permeability and oral bioavailability. In addition, due to their high stability and mutability, the polypeptides can be used as starting points in a library-based approach to find binders for molecules of interest.

As used herein, a macrocyclic polypeptide means a cyclic peptide of 7 to 14 amino acids in length. In various embodiments, the polypeptide may be 7-14, 7-13, 7-12, 7-11, 7-10, 7-9, 7-8, 8-14, 8-13, 8-12, 8-11, 8-10, 8-9, 9-14, 9-13, 9-12, 9-11, 9-10, 10-14, 10-13, 10-12, 10-11, 11-14, 11-13, 11-12, 12-14, 12-13, 13-14, 7, 8, 9, 10, 11, 12, 13, or 14 amino acids in length. The polypeptides of the disclosure are N-to-C cyclized.

As will be understood by those of skill in the art, the polypeptides may be linked to other moieties (linkers, dyes, purification tags, peptides, small molecules, nucleic acids, etc.) as deemed appropriate for an intended use.

As used herein, a mirror image is a polypeptide with the same primary amino acid sequence as the reference sequence, but wherein each residue that is an L amino acid in the reference sequence is a D amino acid in the mirror image polypeptide, and wherein each residue that is an D amino acid in the reference sequence is an L amino acid in the mirror image polypeptide. A polypeptide and its mirror image share similar chemical and physical properties. The only difference is the chirality of the molecule.

In one embodiment, the polypeptide has at least one proline residue. In other embodiments, the peptides have at least 2, 3, or 4 proline residues. In one embodiment, a polypeptide of 7 amino acids in length has 0, 1, or 2 proline residues. In another embodiment, a polypeptide of 8 amino acids in length has 0, 1, or 2 proline residues. In another embodiment, a polypeptide of 9 amino acids in length has 0, 1, 2, 3, or 4 proline residues. In a further embodiment, a polypeptide of 10 amino acids in length has 0, 1, 2, 3, or 4 proline residues. In one embodiment, a polypeptide of 12 amino acids in length has 3 proline residues. In another embodiment, a polypeptide of 14 amino acids in length has 3 proline residues.

In one embodiment, the polypeptide has at least 2 D amino acids. In various further embodiments, the polypeptide has at least 3, 4, 5, 6, 7, 8, or more D amino acids. In one embodiment, a polypeptide of 7 amino acids in length has 2, 3, 4, or 5 D amino acids. In another embodiment, a polypeptide of 8 amino acids in length has 2, 3, 4, 5, or 6 D amino acids. In a further embodiment, a polypeptide of 9 amino acids in length has 2, 3, 4, 5, 6, or 7 D amino acids. In another embodiment, a polypeptide of 10 amino acids in length has 2, 3, 4, 5, 6, 7, or 8 D amino acids. In one embodiment, a polypeptide of 11 amino acids in length has 2, 3, 4, 5, 6, 7, 8, or 9 D amino acids. In another embodiment, a polypeptide of 12 amino acids in length has 2, 3, 4, 5, 6, 7, 8, 9, or 10 D amino acids. In one embodiment, a polypeptide of 13 amino acids in length has 2, 3, 4, 5, 6, 7, 8, 9, 10, or 12 D amino acids. In another embodiment, a polypeptide of 14 amino acids in length has 2, 3, 4, 5, 6, 7, 8, 9, 10, 11, or 12 D amino acids.

In another embodiment, the polypeptides have no more than 3 amino acid substitutions compared to the amino acid sequence of any one of SEQ ID NO: 1-237 or a mirror image thereof. As shown in the examples that follow, the polypeptides of the disclosure are very amenable to mutation while maintaining structural stability and are highly protease stable. The amino acid substitutions may be any natural or unnatural amino acid. In other embodiments, the polypeptides have no more than 2 or 1 amino acid substitutions compared to the amino acid sequence of any one of SEQ ID NO: 1-237 or a mirror image thereof; in another embodiment, the polypeptides comprise or consist of the amino acid sequence of any one of SEQ ID NO: 1-237 or a mirror image thereof.

The amino acid substitutions may be any natural or unnatural amino acid. In one embodiment each amino acid substitution occurs at a non-proline position relative to the reference polypeptide. In a further embodiment, the amino acid substitutions do not include any non-proline residues being substituted to proline. In another embodiment, each amino acid substitution maintains the chirality of the amino acid replaced (i.e.: a D amino acid is replaced by a D amino acid or an L amino acid is replaced with an L amino acid). In a further embodiment, each amino acid substitution is an alpha amino acid (i.e.: amino acids having both the amine and the carboxylic acid groups attached to the first (alpha) carbon atom, which can be in L or D form, or glycine); this group includes all of the naturally occurring amino acids, selenocysteine, and pyrrolysine, and any unnatural amino acid that shares this backbone configuration.

Macrocyclic Polypeptides Designed as Described in the Examples: D Amino Acids Include a "D" Prior to the 3 Letter Amino Acid Abbreviation; L Amino Acids Just Show the 3 Letter Amino Acid Abbreviation 7-mers

| | | |
|---|---|---|
| c.10.2.pdb | DHIS-PRO-DASP-DGLN-DSER-DGLU-PRO | (SEQ ID NO: 1) |
| c.11.18.pdb | DARG-DLYS-PRO-DPRO-ASP-GLU-ASP | (SEQ ID NO: 2) |
| c.2.8.pdb | PRO-ASN-DSER-DGLU-PRO-ASN-DASN | (SEQ ID NO: 3) |
| c.3.100.pdb | DTHR-LYS-DASN-DASP-DTHR-ASN-PRO | (SEQ ID NO: 4) |
| c.3.45.pdb | GLU-ASP-PRO-ARG-DLYS-TYR-DPRO | (SEQ ID NO: 5) |
| c.4.35.pdb | DASP-ARG-GLN-PRO-DPRO-DASP-ASN | (SEQ ID NO: 6) |
| c.4.59.pdb | DASP-DGLN-ASN-DGLU-DASN-PRO-PRO | (SEQ ID NO: 7) |

-continued

| | | |
|---|---|---|
| c.4.78.pdb | PRO-DASN-DTHR-ASN-DGLU-DASN-PRO | (SEQ ID NO: 8) |
| c.5.4.pdb | GLN-ALA-PRO-ASP-DASN-ASN-DASP | (SEQ ID NO: 9) |
| c.8.1.pdb | ASN-DLYS-DARG-PRO-DTHR-DASP-LYS | (SEQ ID NO: 10) |
| c.9.2.pdb | ASP-DGLN-DASP-ARG-ARG-PRO-DPRO | (SEQ ID NO: 11) |

8 mer

| | | |
|---|---|---|
| c.12.43.pdb | LYS-DTYR-DPRO-ASN-ASP-DGLN-DPRO-ASN | (SEQ ID NO: 12) |
| c.15.21.pdb | DARG-GLU-DPRO-DGLN-ARG-DGLU-PRO-GLN | (SEQ ID NO: 13) |
| c.16.34.pdb | PRO-ARG-ALA-DGLN-DTYR-PRO-ASP-DGLU | (SEQ ID NO: 14) |
| c.16.48.pdb | PRO-ARG-ALA-DVAL-DHIS-GLU-ASP-DPRO | (SEQ ID NO: 15) |
| c.17.51.pdb | DASP-GLU-DPRO-DGLN-GLU-DPRO-DASN-ASN | (SEQ ID NO: 16) |
| c.18.79.pdb | PRO-DSER-DGLN-PRO-ARG-HIS-DLYS-DHIS | (SEQ ID NO: 17) |
| c.2.47.pdb | DASP-DASN-DPRO-ASP-ASN-DASP-LYS-ASN | (SEQ ID NO: 18) |
| c.21.27.pdb | TYR-DASP-GLN-DLEU-DPRO-PRO-LEU-DLYS | (SEQ ID NO: 19) |
| c.24.83.pdb | ASP-GLU-PRO-ASN-DGLN-LYS-ASP-DASN | (SEQ ID NO: 20) |
| c.28.17.pdb | DASN-ASP-ALA-PRO-DPRO-DALA-LYS-HIS | (SEQ ID NO: 21) |
| c.28.65.pdb | DARG-DASP-GLU-ASP-PRO-ARG-DARG-ASP | (SEQ ID NO: 22) |
| c.29.21.pdb | GLU-DTYR-PRO-DSER-DPRO-DTHR-DSER-DASN | (SEQ ID NO: 23) |
| c.29.5.pdb | DASN-ASN-ASP-DGLU-DPRO-DHIS-ARG-LYS | (SEQ ID NO: 24) |
| c.4.31.pdb | PRO-LYS-DTHR-DGLU-PRO-ALA-DTHR-DASN | (SEQ ID NO: 25) |
| c.43.15.pdb | DGLN-GLU-DALA-PRO-GLN-DASP-DPRO-DASN | (SEQ ID NO: 26) |
| c.43.64.pdb | DLYS-LYS-DTHR-DGLU-PRO-DGLU-DGLU-DPRO | (SEQ ID NO: 27) |
| c.44.97.pdb | DTHR-ASN-DASP-GLU-ALA-PRO-DSER-DPRO | (SEQ ID NO: 28) |
| c.45.36.pdb | DGLU-PRO-DALA-DLYS-ASP-DLYS-DHIS-LYS | (SEQ ID NO: 29) |
| c.5.40.pdb | DLYS-DVAL-PRO-DASP-DGLN-DILE-PRO-DASN | (SEQ ID NO: 30) |
| c.64.23.pdb | DSER-LYS-GLU-LYS-DTHR-ASP-DPRO-GLU | (SEQ ID NO: 31) |
| t1c.164.98.pdb | ASP-ASP-PRO-THR-DPRO-DARG-GLN-DGLN; also referred to as design 8.1 | (SEQ ID NO: 32) |

9 mer

| | | |
|---|---|---|
| t6c.105.6.pdb | ASP-ASN-LYS-DASP-HIS-DPRO-ASN-ASP-DLYS | (SEQ ID NO: 33) |

-continued

| | | |
|---|---|---|
| t6c.109.55.pdb | DHIS-LYS-DSER-DPRO-DSER-DLYS-SER-DGLU-ASP | (SEQ ID NO: 34) |
| t6c.11.47.pdb | DILE-DPRO-PRO-DVAL-ILE-GLU-DASN-DASP-GLN | (SEQ ID NO: 35) |
| t6c.11.93.pdb | PRO-DARG-LYS-DLEU-DPRO-ASP-GLU-DGLN-DSER | (SEQ ID NO: 36) |
| t6c.111.45.pdb | PRO-DSER-DASN-GLU-DARG-ASP-ASP-DTHR-GLN | (SEQ ID NO: 37) |
| t6c.112.7.pdb | GLN-PHE-PRO-DASP-THR-DLYS-ASP-DALA-DASP | (SEQ ID NO: 38) |
| t6c.112.74.pdb | DARG-DALA-DPRO-PRO-LYS-PRO-DASP-LYS-DASP | (SEQ ID NO: 39) |
| t6c.116.43.pdb | VAL-DGLN-PRO-DPRO-ALA-DTHR-ASP-GLU-SER | (SEQ ID NO: 40) |
| t6c.125.31.pdb | DPRO-ALA-DGLU-PRO-ASN-DTHR-DLYS-SER-PRO | (SEQ ID NO: 41) |
| t6c.129.81.pdb | DGLN-GLN-PRO-DILE-DPRO-ASP-DALA-ASP-ASP | (SEQ ID NO: 42) |
| t6c.136.68.pdb | GLN-HIS-PRO-DGLU-PRO-PRO-SER-LEU-DASP | (SEQ ID NO: 43) |
| t6c.14.12.pdb | HIS-ALA-DGLN-ASP-ASN-DASP-DPRO-DSER-DLYS | (SEQ ID NO: 44) |
| t6c.14.24.pdb | DASP-DASN-LYS-SER-DGLN-ASP-ASN-DVAL-DASP | (SEQ ID NO: 45) |
| t6c.154.74.pdb | DPRO-THR-DTHR-GLU-LYS-ASP-DVAL-PRO-DGLN | (SEQ ID NO: 46) |
| t6c.168.7.pdb | PRO-DASN-DASP-ALA-PRO-DPRO-GLU-PRO-LEU | (SEQ ID NO: 47) |
| t6c.171.34.pdb | PRO-PRO-DTHR-ALA-PRO-DPRO-DASP-ASP-DLYS | (SEQ ID NO: 48) |
| t6c.18.44.pdb | DGLU-DASN-PRO-DPRO-DILE-DALA-DPRO-ASP-ASN | (SEQ ID NO: 49) |
| t6c.183.50.pdb | DPRO-DASN-ASP-DSER-DASP-LYS-PRO-DASN-DSER | (SEQ ID NO: 50) |
| t6c.187.12.pdb | DVAL-DASP-ASP-DASP-HIS-PRO-DARG-DPRO-ASN | (SEQ ID NO: 51) |
| t6c.22.15.pdb | DASP-LYS-DTHR-DASN-ASP-PRO-DPRO-ALA-LYS | (SEQ ID NO: 52) |
| t6c.23.91.pdb | PRO-DPRO-SER-DSER-DSER-DASN-LYS-DSER-DARG | (SEQ ID NO: 53) |
| t6c.238.6.pdb | DPRO-ASN-TYR-DHIS-PRO-LYS-ASP-LEU-DGLN | (SEQ ID NO: 54) |
| t6c.244.59.pdb | DTHR-GLN-DASN-ASN-DASP-DPRO-DARG-DSER-SER | (SEQ ID NO: 55) |
| t6c.26.74.pdb | PRO-DASN-DASP-GLN-DPRO-ASN-DLYS-GLU-HIS | (SEQ ID NO: 56) |
| t6c.26.78.pdb | DPRO-PRO-DASP-ASP-DASP-LYS-PRO-DASN-LYS | (SEQ ID NO: 57) |
| t6c.31.88.pdb | DPRO-LYS-ASP-DTHR-DASP-GLN-GLU-DPRO-GLU | (SEQ ID NO: 58) |
| t6c.32.76.pdb | PRO-DPRO-DTYR-DPRO-ASP-SER-ARG-DILE-ALA | (SEQ ID NO: 59) |
| t6c.32.9.pdb | DVAL-LEU-ASP-ASP-SER-DVAL-VAL-DPRO-PRO | (SEQ ID NO: 60) |

-continued

| | | (SEQ ID NO: 61) |
|---|---|---|
| t6c.33.60.pdb | PRO-DGLU-SER-DALA-LYS-DASP-ASP-DLEU-DASN | |
| | | (SEQ ID NO: 62) |
| t6c.33.8.pdb | DPRO-GLU-DTHR-DLYS-DPRO-ASN-VAL-DVAL-PRO | |
| | | (SEQ ID NO: 63) |
| t6c.38.39.pdb | DALA-DLYS-HIS-DASN-HIS-ASP-DLYS-ASP-ASN | |
| | | (SEQ ID NO: 64) |
| t6c.40.21.pdb | LYS-DGLN-DASP-PRO-DARG-HIS-ASP-DLYS-ASP | |
| | | (SEQ ID NO: 65) |
| t6c.40.92.pdb | DSER-TYR-DGLN-ASP-ASN-DALA-DILE-ASN-DTHR | |
| | | (SEQ ID NO: 66) |
| t6c.54.36.pdb | DGLN-DPRO-ASN-VAL-DASP-LYS-DASP-DASN-THR | |
| | | (SEQ ID NO: 67) |
| t6c.54.87.pdb | ASP-DVAL-PRO-DPRO-ALA-DGLU-ARG-PRO-DPRO | |
| | | (SEQ ID NO: 68) |
| t6c.54.93.pdb | DPRO-DASP-ASN-DVAL-PRO-DPRO-THR-DVAL-DLYS | |
| | | (SEQ ID NO: 69) |
| t6c.58.11.pdb | VAL-DARG-PRO-DSER-VAL-DGLN-DGLU-DPRO-DASN | |
| | | (SEQ ID NO: 70) |
| t6c.6.97.pdb | ALA-PRO-DSER-DALA-ASP-DGLN-DASN-DPRO-ASN | |
| | | (SEQ ID NO: 71) |
| t6c.61.79.pdb | VAL-PRO-ASP-DARG-DVAL-LEU-PRO-DASN-DTYR | |
| | | (SEQ ID NO: 72) |
| t6c.62.76.pdb | DTHR-DASP-DGLN-ASP-GLU-PRO-DTHR-LYS-GLU | |
| | | (SEQ ID NO: 73) |
| t6c.76.60.pdb | ASP-PRO-ASN-DLYS-ASP-ASP-ARG-DTHR-DTYR | |
| | | (SEQ ID NO: 74) |
| t6c.8.39.pdb | DPRO-ASP-ASN-DSER-PRO-THR-GLN-DGLN-DTYR | |
| | | (SEQ ID NO: 75) |
| t6c.80.74.pdb | DSER-DPRO-DSER-ASP-DGLN-ASP-SER-SER-SER | |
| | | (SEQ ID NO: 76) |
| t6c.81.48.pdb | DILE-DPRO-ASP-DARG-THR-DASP-DASP-SER-LYS | |
| | | (SEQ ID NO: 77) |
| t6c.83.33.pdb | DPRO-ASN-GLN-DASN-GLN-DASP-DLEU-DPRO-DILE | |
| | | (SEQ ID NO: 78) |
| t6c.85.94.pdb | ASP-DGLU-DPRO-ASN-DGLN-PRO-DASN-ASP-DASP | |
| | | (SEQ ID NO: 79) |
| t6c.9.57.pdb | PRO-DTHR-DASP-ASP-GLU-DASN-THR-DLYS-HIS | |
| | | (SEQ ID NO: 80) |
| t6c.9.91.pdb | GLU-DLYS-ASN-SER-ASN-DGLU-LYS-PRO-DPRO | |
| | | (SEQ ID NO: 81) |
| t6c.96.89.pdb | DPRO-DASP-GLN-TYR-DARG-ASP-DPRO-TYR-DASP | |

10 mer

| | | (SEQ ID NO: 82) |
|---|---|---|
| c.100.22.pdb | DASP-DASP-DGLU-LYS-DLYS-ASN-DGLU-PRO-ASP-DALA | |
| | | (SEQ ID NO: 83) |
| c.100.72.pdb | DGLN-DGLU-DASP-ARG-DTHR-DGLU-DGLU-PRO-ARG-DARG | |
| | | (SEQ ID NO: 84) |
| c.1003.22.pdb | DTYR-PRO-ALA-DGLN-DPRO-PRO-DLEU-LEU-DLYS-ASP | |
| | | (SEQ ID NO: 85) |
| c.102.56.pdb | DASN-DLYS-DGLU-DLYS-DASP-LYS-ALA-PRO-DGLU-PRO | |
| | | (SEQ ID NO: 86) |
| c.1032.1.pdb | DGLU-DPRO-ASP-DLYS-PRO-DASN-ALA-ASP-DGLN-DGLN | |

-continued

| | | |
|---|---|---|
| c.105.20.pdb | DGLN-DPRO-ASN-DALA-DASP-LYS-ALA-DGLU-DVAL-PRO | (SEQ ID NO: 87) |
| c.105.97.pdb | ASN-DSER-DLYS-DASP-ASP-DTHR-DGLU-PRO-DASN-DPRO | (SEQ ID NO: 88) |
| c.1056.21.pdb | DPRO-GLU-PRO-DGLU-DPRO-DVAL-PRO-ALA-DLYS-DALA | (SEQ ID NO: 89) |
| c.106.6.pdb | DPRO-DARG-DALA-LYS-LEU-PRO-DASN-DSER-DASP-ALA | (SEQ ID NO: 90) |
| c.107.22.pdb | GLU-DPRO-PRO-ASN-ALA-LYS-ASP-DASN-ASN-ALA | (SEQ ID NO: 91) |
| c.107.77.pdb | LYS-DASP-GLN-DPRO-PRO-GLN-ARG-LYS-ASP-DASN | (SEQ ID NO: 92) |
| c.1078.20.pdb | DARG-DASP-LYS-ASP-DLYS-DGLU-PRO-DPRO-ASP-DALA | (SEQ ID NO: 93) |
| c.109.44.pdb | DGLU-DASN-PRO-ALA-DLYS-LYS-PRO-DASP-DHIS-LYS | (SEQ ID NO: 94) |
| c.1095.10.pdb | LYS-ASN-DPRO-PRO-PRO-DTHR-DGLU-PRO-ALA-ALA | (SEQ ID NO: 95) |
| c.110.32.pdb | DALA-DPRO-ASN-TYR-DSER-DLYS-ASP-ASN-DPRO-DLYS | (SEQ ID NO: 96) |
| c.110.61.pdb | LEU-PRO-ARG-DGLN-DPRO-ASN-ASP-DSER-DLYS-DTHR | (SEQ ID NO: 97) |
| c.110.87.pdb | GLU-DPRO-DASN-DSER-DGLU-DPRO-ASN-DASP-DSER-DASN | (SEQ ID NO: 98) |
| c.111.100.pdb | DLYS-DASP-DASN-ASP-PRO-ASN-ASN-DLYS-DLEU-ASP | (SEQ ID NO: 99) |
| c.111.82.pdb | PRO-DASN-GLU-PRO-LYS-TYR-DLYS-DASN-ASP-DGLU | (SEQ ID NO: 100) |
| c.112.45.pdb | ALA-LYS-ASP-DLYS-ASP-ASN-LYS-DASP-PRO-LYS | (SEQ ID NO: 101) |
| c.112.88.pdb | GLN-GLN-DASP-DASP-LYS-ASP-GLN-PRO-DPRO-ASP | (SEQ ID NO: 102) |
| c.113.66.pdb | DGLU-DGLU-PRO-LYS-DILE-PRO-ASP-DLYS-DGLU-DILE | (SEQ ID NO: 103) |
| c.114.4.pdb | DPRO-ASP-DVAL-LYS-PRO-DPRO-GLU-DLEU-LYS-PRO | (SEQ ID NO: 104) |
| c.1143.27.pdb | GLU-GLU-DSER-DPRO-DSER-DSER-DPRO-ASN-DTHR-ASP | (SEQ ID NO: 105) |
| c.115.8.pdb | LYS-ASP-DGLN-DPRO-LYS-DASN-PRO-DASP-DGLN-PHE | (SEQ ID NO: 106) |
| c.1178.14.pdb | ARG-TYR-DSER-TRP-DARG-DASP-PRO-TYR-DGLN-PRO | (SEQ ID NO: 107) |
| c.1181.8.pdb | DTYR-ASP-PRO-ARG-DASP-DSER-DLYS-GLN-DPRO-ASN | (SEQ ID NO: 108) |
| c.1187.26.pdb | ASN-DTYR-DPRO-ASP-PRO-ARG-DTYR-DPRO-ASP-PRO | (SEQ ID NO: 109) |
| c.119.73.pdb | GLN-ARG-ASN-HIS-DPRO-ASP-DTHR-GLN-DPRO-ASP | (SEQ ID NO: 110) |
| c.12.37.pdb | DLEU-GLN-DTHR-DARG-PRO-DSER-ALA-GLU-PRO-DASP | (SEQ ID NO: 111) |
| c.120.11.pdb | GLN-DTYR-LYS-HIS-DASP-HIS-PRO-DHIS-PRO-DASP | (SEQ ID NO: 112) |
| c.120.33.pdb | ALA-ASN-DASN-HIS-PRO-DASN-ALA-DASP-PRO-DALA | (SEQ ID NO: 113) |

-continued

```
                                                          (SEQ ID NO: 114)
c.1215.1.pdb      DGLN-DPRO-DTHR-ASN-DILE-DPRO-ASN-DASP-GLU-ASP (SEQ ID NO: 115)
c.128.3.pdb       DLYS-ASP-ASN-DPRO-ASN-DALA-DASP-PRO-DLYS-ASP (SEQ ID NO: 116)
c.129.40.pdb      PRO-DARG-DASP-GLN-GLU-DPRO-ASN-DSER-DSER-DASN (SEQ ID NO: 117)
c.1299.4.pdb      LEU-DVAL-ARG-DASN-HIS-PRO-DPRO-ASP-DGLU-ASN (SEQ ID NO: 118)
c.137.2.pdb       DGLN-DALA-PRO-ASN-LYS-DARG-LYS-DPRO-ASP-ASP (SEQ ID NO: 119)
c.138.17.pdb      ALA-PRO-DSER-DILE-GLN-PRO-ASN-DGLU-DASN-ASN (SEQ ID NO: 120)
c.140.60.pdb      ASN-ASN-DLYS-ASP-ASN-DASP-PRO-ALA-DARG-PRO (SEQ ID NO: 121)
c.142.41.pdb      PRO-DPRO-GLU-DALA-DARG-GLU-GLU-DPRO-DALA-DGLN (SEQ ID NO: 122)
c.143.37.pdb      DTYR-DPRO-HIS-PRO-DASN-DTYR-GLU-ASP-LYS-ASP (SEQ ID NO: 123)
c.143.85.pdb      DGLN-DPRO-ASP-PRO-ASN-DVAL-GLU-MET-LYS-ASP (SEQ ID NO: 124)
c.145.1.pdb       ASP-PRO-DASN-DLYS-LYS-GLU-DASP-GLU-ASN-DSER (SEQ ID NO: 125)
c.145.61.pdb      DASN-DALA-GLN-ASP-DASN-PRO-DGLU-DPRO-LYS-PRO (SEQ ID NO: 126)
c.146.71.pdb      DPRO-ASP-GLN-DASP-ASP-PRO-ARG-ARG-DSER-DALA (SEQ ID NO: 127)
c.148.21.pdb      DHIS-ASN-DSER-GLU-ALA-DASN-PRO-ASN-ARG-DALA (SEQ ID NO: 128)
c.148.33.pdb      DASN-ASP-DGLN-DLYS-DASP-ASN-DSER-DGLU-PRO-PRO (SEQ ID NO: 129)
c.148.90.pdb      GLU-TYR-DPRO-DLYS-DSER-ALA-ALA-PRO-LYS-DGLN (SEQ ID NO: 130)
c.15.52.pdb       PRO-DHIS-DPRO-ASN-ASP-DVAL-ASN-ASN-DASN-ARG (SEQ ID NO: 131)
c.151.53.pdb      DTYR-DPRO-ASP-TYR-DILE-DPRO-ASP-ASP-ARG-TYR (SEQ ID NO: 132)
c.153.54.pdb      DSER-LYS-DASP-ALA-PRO-GLU-DGLU-PRO-ARG-ARG (SEQ ID NO: 133)
c.154.1.pdb       LYS-DGLU-PRO-DSER-DSER-DALA-DGLU-PRO-ASN-DASP (SEQ ID NO: 134)
c.155.55.pdb      DSER-DPRO-DALA-LYS-DPRO-DASN-DSER-GLN-PRO-DASN (SEQ ID NO: 135)
c.157.24.pdb      ASP-ASN-LYS-DASN-PRO-DPRO-DASP-DGLN-DSER-DGLN (SEQ ID NO: 136)
c.157.39.pdb      ASP-DSER-PRO-ASN-LEU-DSER-DASP-GLN-DGLN-DPRO (SEQ ID NO: 137)
c.157.61.pdb      ASP-DSER-PRO-ASN-LEU-ASN-LYS-ASP-DVAL-DPRO (SEQ ID NO: 138)
c.157.63.pdb      DTHR-DGLU-PRO-DGLN-DSER-GLU-DPRO-PRO-ASN-LEU (SEQ ID NO: 139)
c.158.36.pdb      ASP-DGLU-DALA-DPRO-ASN-LYS-DGLU-DARG-DPRO-ASN (SEQ ID NO: 140)
c.159.6.pdb       ASN-DLYS-LEU-PRO-PRO-DASP-ALA-DTHR-DASN-DGLU
```

-continued

```
                                                            (SEQ ID NO: 141)
c.16.12.pdb         DARG-DLYS-DGLU-PRO-DALA-GLU-ASP-DASN-PRO-ASN (SEQ ID NO: 142)
c.16.3.pdb          PRO-ASN-DARG-DTHR-DGLU-PRO-DALA-GLU-TYR-DASP (SEQ ID NO: 143)
c.16.31.pdb         DLEU-DPRO-GLU-DPRO-DTYR-ALA-LEU-DLYS-PRO-ASN (SEQ ID NO: 144)
c.161.54.pdb        LYS-DSER-PRO-DPRO-DASN-ASP-ASN-LYS-ASP-DVAL (SEQ ID NO: 145)
c.161.55.pdb        DVAL-PRO-ASP-HIS-ASN-DASN-PRO-ASP-HIS-ASN (SEQ ID NO: 146)
c.164.11.pdb        LYS-GLU-DVAL-DPRO-ASN-DTHR-DSER-DPRO-DSER-DALA (SEQ ID NO: 147)
c.164.35.pdb        DTHR-DASP-DASP-ASP-DGLN-ALA-DILE-DPRO-PRO-DVAL (SEQ ID NO: 148)
c.165.18.pdb        DLYS-DARG-LYS-DLEU-DPRO-GLU-PRO-DGLU-GLU-DALA (SEQ ID NO: 149)
c.165.81.pdb        GLU-DPRO-ASP-DSER-DSER-DASN-GLU-DTYR-PRO-DARG (SEQ ID NO: 150)
c.17.74.pdb         ASP-LYS-DLYS-DLEU-ALA-PRO-DASN-DASP-ASP-PRO (SEQ ID NO: 151)
c.175.67.pdb        DPRO-DALA-DSER-ASP-PRO-ARG-DARG-GLU-DGLN-PRO (SEQ ID NO: 152)
c.177.32.pdb        GLU-DALA-DLYS-ASP-DVAL-DPRO-ASP-ASN-MET-DPRO (SEQ ID NO: 153)
c.180.41.pdb        MET-ASN-LYS-DLYS-PRO-DASP-ALA-DTHR-PRO-ASP (SEQ ID NO: 154)
c.185.87.pdb        ALA-DGLN-TYR-PRO-DASP-GLN-DARG-DGLN-PRO-ALA (SEQ ID NO: 155)
c.186.82.pdb        PRO-DHIS-LYS-GLN-PRO-DASP-DASP-ASN-DASN-GLU (SEQ ID NO: 156)
c.187.91.pdb        DASP-ALA-PRO-DPRO-ASN-ASP-DASP-DASN-PRO-DSER (SEQ ID NO: 157)
c.19.76.pdb         DLYS-ASN-DASN-DASP-GLN-DASP-DLYS-TYR-PRO-DPRO (SEQ ID NO: 158)
c.191.37.pdb        ASN-DVAL-ASN-PRO-DTYR-DPRO-ASP-DALA-DPRO-DPRO (SEQ ID NO: 159)
c.195.98.pdb        GLN-DPRO-DPRO-ASN-DALA-PRO-LYS-GLU-DSER-DSER (SEQ ID NO: 160)
c.2.21.pdb          ASN-DALA-PRO-ASN-DTHR-DSER-DASP-GLU-ASN-DLYS (SEQ ID NO: 161)
c.20.98.pdb         GLN-DGLU-PRO-DPRO-ALA-DALA-DALA-GLN-DASP-DLYS (SEQ ID NO: 162)
c.200.97.pdb        ASP-DSER-DPRO-DSER-DASN-ASP-PRO-ARG-HIS-DASP (SEQ ID NO: 163)
c.201.15.pdb        DVAL-ASP-HIS-LYS-DGLN-PRO-DPRO-ALA-DLYS-GLU (SEQ ID NO: 164)
c.205.19.pdb        DSER-DPRO-DSER-DLYS-ASP-DLYS-DASP-ASN-ALA-PRO (SEQ ID NO: 165)
c.206.81.pdb        DARG-DPRO-ASP-DASP-PRO-ASN-DASP-DLYS-DARG-ASP (SEQ ID NO: 166)
c.206.85.pdb        ALA-LEU-DGLU-PRO-ASN-DSER-DPRO-DSER-GLU-DSER (SEQ ID NO: 167)
c.212.79.pdb        DSER-ASP-DGLN-TYR-DPRO-ASN-DALA-DPRO-ASP-ASP
```

-continued

| | | |
|---|---|---|
| c.213.68.pdb | DGLU-DALA-ARG-ASP-HIS-LYS-DVAL-PRO-DPRO-ALA | (SEQ ID NO: 168) |
| c.217.29.pdb | GLN-ASP-ASN-DLYS-ASP-DGLN-ASP-ASN-PRO-ASP | (SEQ ID NO: 169) |
| c.217.71.pdb | TYR-PRO-GLU-ALA-LYS-ASP-DASN-ASN-LYS-DASP | (SEQ ID NO: 170) |
| c.22.67.pdb | PRO-ASP-DTHR-DARG-DASP-ALA-DGLN-ASP-ARG-DILE | (SEQ ID NO: 171) |
| c.223.66.pdb | LYS-PRO-GLN-GLU-DPRO-PRO-DASP-ALA-ASN-LYS | (SEQ ID NO: 172) |
| c.224.14.pdb | ASP-DVAL-ASP-PRO-DGLU-DHIS-DPRO-ASN-DALA-DLYS | (SEQ ID NO: 173) |
| c.225.68.pdb | GLU-DPRO-ASN-DASP-DPRO-ASN-DASN-DGLU-PRO-DVAL | (SEQ ID NO: 174) |
| c.229.8.pdb | DPRO-ASN-DASP-DGLU-PRO-ASP-LYS-DASP-ARG-DHIS | (SEQ ID NO: 175) |
| c.231.18.pdb | DSER-GLU-DPRO-DGLN-GLN-DSER-GLU-DPRO-DALA-TYR | (SEQ ID NO: 176) |
| c.234.57.pdb | DPRO-ALA-DASP-HIS-LYS-ASN-DARG-LYS-DGLU-PRO | (SEQ ID NO: 177) |
| c.24.60.pdb | DASP-ASP-DGLN-LEU-PRO-DASP-DVAL-PRO-ASN-ALA | (SEQ ID NO: 178) |
| c.24.90.pdb | DARG-DSER-PRO-GLU-LYS-DSER-DLYS-ASP-LYS-PRO | (SEQ ID NO: 179) |
| c.241.1.pdb | PRO-ASN-LYS-DASP-ASN-DGLU-PRO-ALA-ARG-DGLU | (SEQ ID NO: 180) |
| c.241.69.pdb | PRO-ASN-LYS-DASP-GLN-PRO-DSER-ALA-ASP-DGLU | (SEQ ID NO: 181) |
| c.241.95.pdb | ALA-ASP-DARG-TYR-DASP-DGLU-PRO-MET-PRO-DSER | (SEQ ID NO: 182) |
| c.244.45.pdb | LYS-ASN-DLYS-DSER-DGLU-PRO-PRO-DASP-PRO-ALA | (SEQ ID NO: 183) |
| c.244.98.pdb | ASP-GLU-ARG-PRO-DPRO-LYS-ALA-LYS-ASP-DLYS | (SEQ ID NO: 184) |
| c.257.63.pdb | DALA-ASP-DARG-DASN-ASP-PRO-ARG-ALA-DTHR-DSER | (SEQ ID NO: 185) |
| c.257.93.pdb | GLN-ALA-PRO-DGLU-PRO-PRO-GLU-ALA-DLYS-DASP | (SEQ ID NO: 186) |
| c.264.71.pdb | ASN-DTYR-DGLU-DPRO-HIS-DLYS-DTYR-ASP-DLEU-DPRO | (SEQ ID NO: 187) |
| c.265.16.pdb | DTHR-PRO-LYS-DTHR-ASP-DLYS-ASP-ARG-DASP-DPRO | (SEQ ID NO: 188) |
| c.268.11.pdb | ALA-DASP-DPRO-DSER-LYS-DGLU-DLEU-DPRO-ASP-DASN | (SEQ ID NO: 189) |
| c.27.32.pdb | DGLU-PRO-DPRO-ALA-LYS-ASP-DHIS-ASN-DASP-ARG | (SEQ ID NO: 190) |
| c.28.81.pdb | ASP-ALA-PRO-LYS-PRO-DSER-DGLN-GLN-DASP-DASN | (SEQ ID NO: 191) |
| c.285.52.pdb | DGLN-ASN-DGLU-ASN-DALA-HIS-GLN-DASP-DPRO-DARG | (SEQ ID NO: 192) |
| c.287.72.pdb | ASN-LYS-DGLN-PRO-DASP-ASN-DTHR-ASN-ASP-DPRO | (SEQ ID NO: 193) |
| c.29.27.pdb | DPRO-DASN-DALA-ASN-GLN-DARG-DPRO-PRO-DASP-GLN | (SEQ ID NO: 194) |

-continued

```
                                                         (SEQ ID NO: 195)
c.29.82.pdb      ASN-DTYR-ASN-DGLU-DASN-DALA-GLN-HIS-DPRO-DPRO (SEQ ID NO: 196)
c.292.61.pdb     DPRO-DVAL-LYS-DASP-DASP-DHIS-PRO-DASN-DASP-GLU (SEQ ID NO: 197)
c.292.81.pdb     DGLN-DASN-DPRO-ASN-ASN-PRO-ARG-DLYS-DALA-ASP (SEQ ID NO: 198)
c.294.7.pdb      ASP-DLYS-ASP-DTYR-DGLU-PRO-DPRO-DTHR-DALA-DHIS (SEQ ID NO: 199)
c.3.70.pdb       ASP-DASN-ALA-PRO-ASN-DASP-LYS-ASP-DGLN-DSER (SEQ ID NO: 200)
c.306.55.pdb     TYR-GLU-DTYR-PRO-DASP-DLEU-DPRO-DILE-PRO-DSER (SEQ ID NO: 201)
c.306.8.pdb      DPRO-PRO-PRO-GLU-ASN-DSER-DLEU-ASP-DGLN-DLEU (SEQ ID NO: 202)
c.31.79.pdb      DASN-GLU-ALA-GLU-PRO-LYS-DSER-DALA-ALA-ASP (SEQ ID NO: 203)
c.310.87.pdb     GLU-PRO-LYS-TYR-DASP-GLN-ASP-MET-ARG-ARG (SEQ ID NO: 204)
c.312.72.pdb     ASP-ASP-PRO-ARG-LYS-DASP-ASP-ALA-GLN-DASP (SEQ ID NO: 205)
c.315.84.pdb     DGLU-DTHR-LYS-DALA-DPRO-DTHR-DGLU-DGLU-PRO-DLYS (SEQ ID NO: 206)
c.326.62.pdb     DGLN-ALA-DARG-GLN-PRO-DPRO-ASP-ALA-ASN-LYS (SEQ ID NO: 207)
c.33.10.pdb      DGLU-PRO-ASN-DVAL-DASN-DGLU-DPRO-DARG-LYS-ALA (SEQ ID NO: 208)
c.33.75.pdb      DSER-DGLU-DPRO-DASP-DASN-LYS-ALA-DLYS-PRO-ASN (SEQ ID NO: 209)
c.33.80.pdb      DALA-LYS-GLU-DGLN-ASP-ALA-DGLN-ALA-PRO-DPRO (SEQ ID NO: 210)
c.334.4.pdb      PRO-ASN-DLYS-ASP-DSER-DPRO-DLYS-LYS-ASP-DVAL (SEQ ID NO: 211)
c.339.46.pdb     DSER-DASP-DSER-DGLN-LYS-PRO-DPRO-LYS-DLEU-ASP (SEQ ID NO: 212)
c.339.9.pdb      DTYR-PRO-TYR-PRO-DASP-DHIS-ALA-ASP-DGLN-LYS (SEQ ID NO: 213)
c.34.5.pdb       DVAL-DPRO-ASN-DTRP-GLU-DPRO-TYR-DGLN-ASP-LYS (SEQ ID NO: 214)
c.34.99.pdb      DLYS-ASP-DALA-DPRO-PRO-ALA-DLYS-ASP-ARG-DASN (SEQ ID NO: 215)
c.340.84.pdb     GLN-ASP-DLYS-GLU-DALA-DPRO-PRO-LYS-ASP-DASP (SEQ ID NO: 216)
c.341.76.pdb     DALA-GLN-DGLU-PRO-ALA-DGLN-ASP-HIS-PRO-DASN (SEQ ID NO: 217)
c.342.15.pdb     GLN-DPRO-DARG-DALA-LYS-ALA-DLYS-DGLU-DPRO-DLYS (SEQ ID NO: 218)
c.344.36.pdb     DASP-DASP-ARG-DLYS-PRO-DGLU-PRO-DLYS-DPRO-ASP (SEQ ID NO: 219)
c.346.38.pdb     ASP-DASP-GLN-PRO-DASP-ASP-DASP-GLN-PRO-DASP (SEQ ID NO: 220)
c.351.67.pdb     DPRO-ASN-DILE-DASP-DPRO-ASP-PRO-ARG-DASN-DARG (SEQ ID NO: 221)
c.352.6.pdb      DGLN-ASP-LYS-GLU-DPRO-DASP-PRO-ASN-ALA-ASP
```

-continued

```
                                                       (SEQ ID NO: 222)
c.356.41.pdb     ASP-DGLU-PRO-ASN-ALA-GLU-DSER-DPRO-DSER-GLN (SEQ ID NO: 223)
c.358.11.pdb     DLYS-DGLU-DLYS-ASP-DLYS-DPRO-ASP-PRO-ARG-GLN (SEQ ID NO: 224)
c.362.67.pdb     DPRO-ASN-ASP-ALA-PRO-DASP-LYS-DASP-DASN-DGLN (SEQ ID NO: 225)
c.369.88.pdb     DGLN-PRO-DASN-DALA-DPRO-LYS-DTHR-GLU-TRP-ALA (SEQ ID NO: 226)
c.38.19.pdb      GLU-DPRO-PRO-ALA-LYS-ASP-ASN-DLYS-DSER-DSER (SEQ ID NO: 227)
11_55            DALA-GLN-DPRO-DCYS-DLYS-ASP-SER-DTYR-DCYS-PRO-DSER (SEQ ID NO: 228)
12_55            HIS-DPRO-DVAL-CYS-DLEU-PRO-DPRO-GLU-DLYS-VAL-CYS-DGLU (SEQ ID NO: 229)
14_55            DPRO-DCYS-ASN-DVAL-DPRO-ASP-VAL-TYR-CYS-DPRO-DASN-LYS-TYR-
                 DVAL
                                                       (SEQ ID NO: 230)
7.1              ASP-THR-DASN-DPRO-THR-DLYS-ASN (SEQ ID NO: 231)
7.2              ASP-GLN-SER-GLU-DPRO-HIS-DPRO (SEQ ID NO: 232)
7.3              GLN-ASP-PRO-DPRO-LYS-DTHR-DASP (SEQ ID NO: 233)
7.4              DLYS-TYR-DPRO-GLU-ASP-GLU-ARG (SEQ ID NO: 234)
8.2              PRO-GLN-DARG-GLN-DPRO-DGLN-ARG-DGLU (SEQ ID NO: 235)
9.1              LYS-ASP-LEU-DGLN-DPRO-PRO-TYR-DHIS-PRO (SEQ ID NO: 236)
10.1             PRO-GLU-ALA-ALA-ARG-DVAL-DPRO-ARG-DLEU-DTHR (SEQ ID NO: 237)
10.2             GLU-DVAL-ASP-PRO-DGLU-DHIS-DPRO-ASN-DALA-DPRO
```

The polypeptides of the disclosure can be made by any suitable technique, including but not limited to the methods disclosed in the examples that follow.

In another embodiment, the disclosure provides polypeptide libraries, comprising two or more polypeptides according to any embodiment or combination of embodiments of the disclosure. The polypeptide libraries can be used for any suitable purpose, including but not limited to screening for suitable polypeptides to serve as scaffolds for therapeutic development. In various embodiments, the libraries comprise 5, 10, 25, 50, 75, 100, 125, 150, 175, 200, 225, 237, 250, 275, 300, 325, 350, 375, 400, 425, 450, 474, 500, 750, 1000, or more of the polypeptides of the disclosure.

The polypeptide libraries may be present in solution or on a solid support including but not limited to a microarray, glass slide, membrane, microplate, beads, or resins. The polypeptides in the library may be labeled with a detectable label. The libraries may be stored frozen, in lyophilized form, or as a solution.

In another embodiment the disclosure provides uses of the polypeptides or polypeptide libraries of any embodiment or combination of embodiments of the disclosure as a scaffold for target-based drug design, or as a starting point in a library-based approach to find binders for molecules of interest.

EXAMPLES

Mixed chirality peptide macrocycles such as cyclosporine are among the most potent therapeutics identified to-date, but there is currently no way to systematically search the structural space spanned by such compounds. Natural proteins do not provide a useful guide: peptide macrocycles lack regular secondary structures and hydrophobic cores and can contain local structures not accessible with L-amino acids. Here we enumerate the stable structures that can be adopted by macrocyclic peptides composed of L- and D-amino acids by near exhaustive backbone sampling followed by sequence design and energy landscape calculations. We identify more than 200 designs predicted to fold into single stable structures, many times more than the number of currently available unbound peptide macrocycle structures. NMR structures of nine of twelve designed 7-10 residue macrocycles, and three 11-14 residue bicyclic designs are close to the computational models. Our results provide a nearly complete coverage of the rich space of structures possible for short peptide macrocycles and vastly increase the available starting scaffolds for both rational drug design and library selection methods.

The high stability, diverse functionality, and favorable pharmacokinetic properties of macrocyclic peptides make them promising starting points for targeted therapeutics (1-4). However, there are few well-characterized natural macrocycles and they are difficult to repurpose for new functions. Designing shorter peptide macrocycles had remained an unsolved challenge. The driving force for the folding of larger peptides and proteins is the sequestration of hydrophobic residues in a non-polar core, enabled by regular secondary structures in which buried backbone polar groups can make hydrogen bonds. This principle has been the basis of almost all previous peptide and protein design work. However, the balance of forces is considerably different for 7-14 residue peptides: they are too small to have either a solvent-excluded hydrophobic core or α-helical and β-sheet (other than β-hairpin) secondary structures. Beyond these differences in the physics of folding, protein design methods often use the PDB (Protein Data Bank) as a source of local structural information, but native structures provide a poor guide for local structures that include non-canonical D-amino acids. On the other hand, short cyclic peptides are an attractive target for computational design as unlike larger systems, there is the possibility of obtaining a completeness of conformational sampling rare in any molecular design endeavor.

The local structure space relevant for cyclic peptides is quite different than that of proteins, so they cannot be systematically generated by assembling protein fragments. Instead, we used generalized kinematic closure (genKIC) methods (15-17) with achiral flat-bottom backbone torsional sampling distributions to generate closed backbone structures starting from a polyglycine chain. For each structure, we used Monte Carlo simulated annealing to search for the lowest energy amino acid sequence, restricting positions with negative values of the backbone torsion angle phi to L-amino acids (and rotamers) and those with positive values to D-amino acids, and disallowing glycine to maximize local sequence encoding of the structure. In preliminary calculations, we found that energy gaps greater than ~10 $k_BT$ (~6 kcal/mol) could only be obtained for N-residue macrocycles if they contained at least N/3 backbone hydrogen bonds; hence in subsequent calculations backbones with fewer hydrogen bonds were discarded. We carried out large scale backbone generation and sequence design calculations for 7-10 residue backbone cyclized peptides, obtaining 50, 596, 12374, 49571 distinct backbones for lengths 7, 8, 9 and 10 respectively after clustering based on backbone torsion angle bins (ABXY, where torsion bin A=the helical region of Ramachandran space, B=extended strand-like region, X=mirror of A, Y=mirror of B) and backbone hydrogen bond patterns. Because the sampling method is stochastic, there is no guarantee of completeness, but the symmetry of the system enables a convergence test: for each distinct peptide backbone conformation identified, the mirror image should also be observed. As the amount of sampling increases, the number of clusters identified for which the mirror image is observed initially increases, as does the number of clusters with no mirror. The former then plateaus, while the latter decreases to near zero. Such convergence suggests near-complete coverage of the combined D- and L-space compatible with peptide closure with backbone hydrogen bonds and no steric clashes. We also sampled and designed structures for 11-14 residue macrocycles, but did not seek completeness due to combinatorial explosion in the number of states.

The Monte Carlo simulated annealing sequence design calculations seek a sequence that minimizes the energy of the target backbone conformation, but there is no guarantee that the sequence found maximizes the energy gap between the target backbone conformation and alternative conformations. To assess the energy landscape for low energy designs (from 21 designs for length 7 to 673 designs for length 10), $10^5$-$10^6$ conformations were generated for each sequence, and the energy minimized with respect to the backbone and sidechain torsion angles. The energy gap and Boltzmann-weighted probability of finding the peptide in or close to the designed main chain conformation ($P_{Near}$) were estimated from the resulting energy landscapes. A total of 12, 22, 45, and 145 designs with distinct backbone structures had energy landscapes strongly funneled into the design target structure for 7, 8, 9 and 10 residue macrocycles respectively Because of the constraints imposed by the cyclic backbone, the small size, and the presence of D-amino acids, the designs span a local structural space inaccessible or underexplored in native proteins. Recurrent features include hydrogen-bonded turn-like structures and proline-stabilized kinks, some of which are observed rarely or not at all in native proteins, that can be viewed as building blocks for designing different macrocycles. Stepwise residue insertion preserves some of the building blocks and alters others, resulting in a complex propagation of features from the shorter macrocycles to the longer ones.

Figure 2:
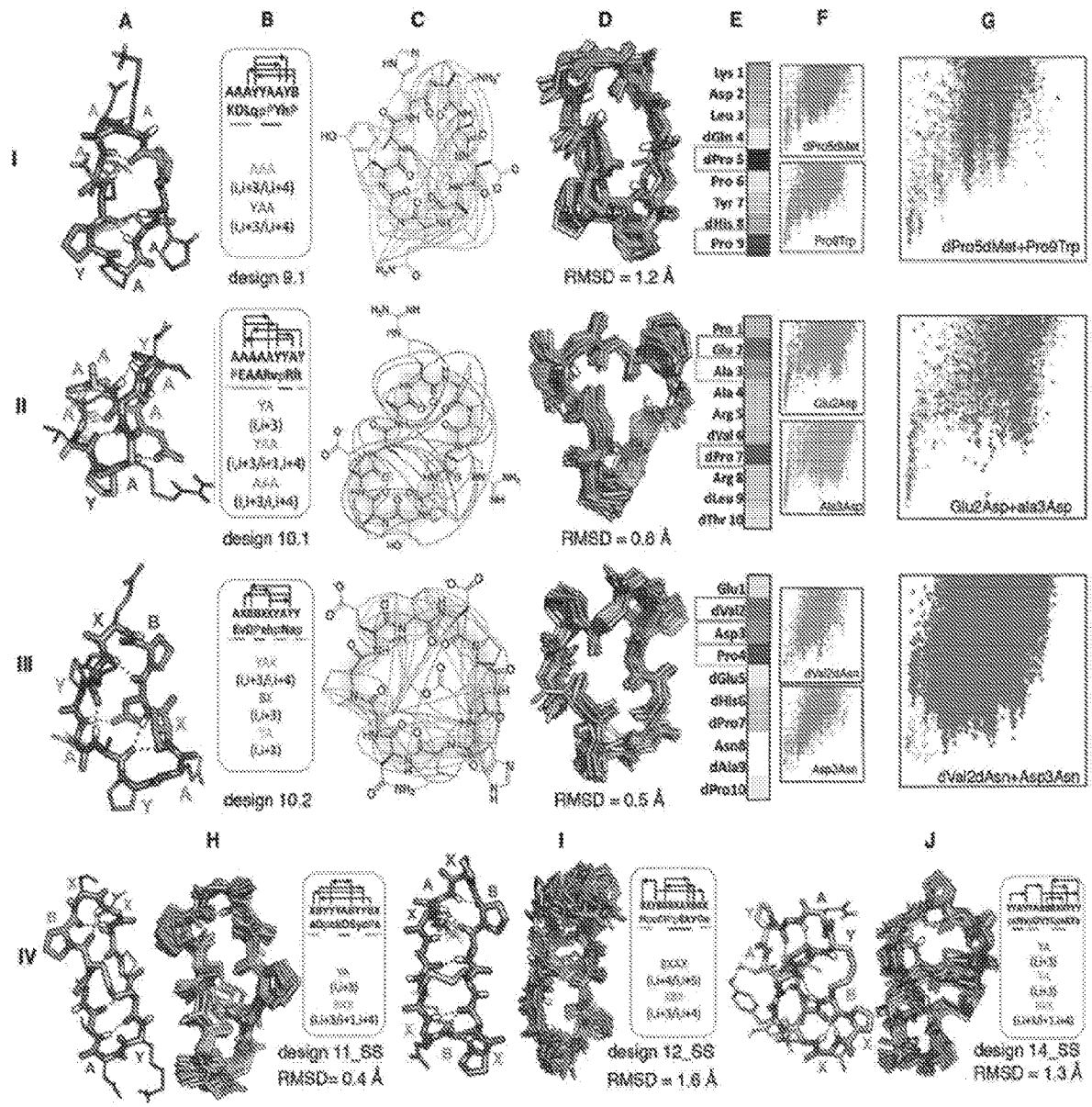
FIG. 2. 9-14 residue macrocycle NMR structures are very close to design models. Rows I-III: 9 and 10 residue designs. Columns A-G are as in FIG. 3 rows II, IV, V. Row IV: Comparison of bicyclic design models and NMR structures.

It was not feasible to characterize each of the 237 macrocycle designs (SEQ ID NOS:1-237) experimentally. Instead we chemically synthesized a subset of 12 peptides (four 7mers: 7.1, 7.2, 7.3, 7.4, two 8mers: 8.1, 8.2, three 9mers: including 9.1, and three 10mers: including 10.1, 10.2), and experimentally characterized their structures by NMR spectroscopy. 10 of the 12 peptides had well-dispersed 1D NMR spectra with the number of backbone HN peaks expected for a single conformation. We collected extensive NOE data (Fig. S11) for these peptides, and solved their structures using XPLOR-NIH (18, 19) followed by NOE restrained molecular dynamics (MD) simulations (very similar structures were obtained with an independent large scale enumeration approach). As shown in FIGS. 1-3 and described below, the experimental NMR structures closely matched the design models for 9 of these peptides, and in unrestrained MD simulations, 8 out of these 9 peptides are within 1 Å of the designed structure over 75% of the time.

Unlike proteins, macrocycles cannot be stabilized primarily by the hydrophobic effect as they are too small to form a core that can exclude solvent (20). How then do the sequences of the designs specify their structures? To address this question, we computed the effect on folding of every single substitution to a different amino acid with the same chirality, and to an alanine with opposite chirality, at each position, for all the designs with NMR confirmed structures. For each of the 20*Nres variants full energy landscape calculations were carried out using the large scale backbone enumeration method described earlier (FIGS. 1 and 2). These computationally intensive calculations were carried out using cellular phones and tablets of volunteers participating in the Rosetta@Home™ distributed computing project. To evaluate the computed sequence-energy landscape experimentally, we used SLIM (Structures For Lossless Ion Manipulations), an ion mobility mass spectrometry technique that can distinguish different conformations in small molecular structures (21). This technique requires only a small amount of unpurified sample, and enables parallel evaluation of the effects of amino acid substitutions on folding. SLIM results from a set of variants with point mutations of design 7.1 at either the dPro4 or dThr5 position (FIG. 1) were consistent with the sequence-energy landscape calculations: the structure was perturbed more by mutations at the dPro4 position than at the dThr5 position, consistent with the computed $P_{Near}$ values.

Several general principles emerge from the comprehensive landscape calculations and from folding calculations on permuted sequences. First, L- and D-proline residues play a key role in structure specification: 52% of the positions in which substitutions disrupt the structure are proline residues in the design, and in almost all of the cases, the most destabilizing mutant of a non-proline residue is a substitution to proline. Proline is the most torsionally constrained amino acid, and placement of L- and D-proline residues favors specific turn and kink structures. Second, sidechain-to-backbone hydrogen bonds that either stabilize a structural motif, such as Asp2 in design 8.1, or connect two sides of the structure, such as Glu2 in design 10.1 or Asp3 in design 10.2, are important for structural specification as removal of these interactions substantially reduces the energy gaps. Third, chirality in many cases plays a greater role in structure specification than sidechain identity: replacing an amino acid residue with its mirror is usually more disruptive than changing to a different amino acid with the same chirality. Fourth, for each design, usually fewer than 3 residues (often proline) are critical to defining the fold, leaving the remainder largely free for future functionalization. Even after mutation of the remaining residues to Ala (retaining chirality) a number of the sequences still encode the designed structure. Overall, this global analysis of the effect of substitutions on energy landscape topography defines the sequence determinants of the folding energy landscape in unprecedented detail.

It is instructive to consider these data in the context of the structures and sequences of the individual designs. The 7-residue macrocycles exhibit several recurrent backbone hydrogen bonding patterns, often featuring a proline-nucleated i,i+3/i,i+4 motif (this motif connects residue 1 and three residues after that with a hydrogen bond and connects residue 1 and fourth residue after that (i+4) with a turn). Of the four 7 residue designs experimentally tested, three had structures nearly identical to the design models (FIG. 1, Table 1), and MD and Rosetta™ calculations on the fourth (design 7.4) suggest it also is close to the design model despite overlap of backbone NH group NOEs. The energy landscape calculations show that the proline nucleating the i,i+3/i,i+4 turn is essential (FIG. 1A, E). The remainder of the structure is largely specified by the designed amino acid chirality with the exception of dPro5 in design 7.2, which packs on the turn-nucleating dPro7. The 8-residue macrocycles are dominated by two major classes, one featuring two i,i+3/i,i+4 motifs, and the other, two criss-cross i,i+3/i+1,i+4 motifs (this motif connects the ith residue and three residues after that (i+3) with a hydrogen bond (I,i+3), and connects residue adjacent to ith residue (i+1) and four residue after residue I (i+4) with a hydrogen bond (I,i+4), resulting in a motif called I,i+3/i+1/i+4) (FIG. 2, third row). The two 8-residue macrocycles that were experimentally characterized both had NMR structures within 1 Å of the design model. Design 8.1 has multiple slow-exchanging sidechain-sidechain and sidechain-backbone hydrogen bonds, with a structurally critical (FIG. 1A, E) hydrogen bond from Asp2 to the backbone of Thr4, which along with Pro3 stabilizes a sharp kink in the chain. Adjacent to the kink is a BXX (i,i+3/i+1,i+4) motif rare in proteins, anchored by the structurally critical dPro5. Design 8.2 has near-perfect sequence inversion symmetry; the sequence symmetric version of this design with sequence PQrEpqRe and torsion string AAYBXXBY, has half the number of NMR resonances (3 backbone HN instead of 6) consistent with structural S2 symmetry. In contrast to the other 7-8 residue designs characterized, all residues in design 8.2 (SEQ ID NO:234) are important for structure specification (FIG. 1E), with residues involved in multiple sidechain-sidechain hydrogen bonds more essential than the two prolines.

TABLE 1

Different structural features observed for experimentally verified designs. (from top to bottom SEQ ID NOs: 230, 231, 232, 233, 32, 234, 235, 236, and 237)

| name | sequence | number of turns | sc-mediated hbond |
|---|---|---|---|
| design 7.1 | Asp-Thr-dAsn-dPro-Thr-dLys-Asn<br>A   A   Y    Y    A   X    B | AA (i,i+3)<br>YAX(i,i+3/I,i+4) | Asn7-Thr2(NH)<br>Asn7-Thr5(C = O) |
| design 7.2 | Asp-Gln-Ser-Glu-dPro-His-dPro<br>A   A   B   B   X    B   Y | BX(i,i+3)<br>YAA(i,i+3/i,i+4) | |
| design 7.3 | Gln-Asp-Pro-dPro-Lys-dThr-dAsp<br>A   B   B   X    A   Y    Y | XA(i,i+3)<br>BXA(i,i+3/i,i+4) | |
| design 7.4 | dLys-Tyr-dPro-Glu-Asp-Glu-Arg<br>X    A   X    A   B   A   A | XA(i,i+3)<br>AAX(i,i+3/i,i+4) | Asp5-Arg(NH)<br>Asp5-Arg |
| design 8.1 | Asp-Asp-Pro-Thr-dPro-dArg-Gln-dGln<br>A   B   A   B   X    X    B   Y | YA(i,i+3)<br>BXX(i,i+3/i+1,i+4) | dArg6-dGln8(C = O)<br>Gln7-dPro5(C = O)<br>Asp2-Thr4(NH) |
| design 8.2 | Pro-Gln-dArg-Gln-dPro-dGln-Arg-dGlu<br>A   A   Y    B   X    X    B   Y | YAA(i,i+3/1+1,i+4)<br>BXX(i,i+3/i+1,i+4) | Gln2-Arg5-Gln4<br>dArg3-dGln6-Glu8 |
| design 9.1 | Lys-Asp-Leu-dGln-dPro-Pro-Tyr-dHis-Pro<br>A   A   A   Y    Y    A   A   Y    B | AAA(i,i+3/i,i+4)<br>YAA(i,i+3/i,i+4) | dGln4-Lys1(C = O) |
| design 10.1 | Pro-Glu-Ala-Ala-Arg-dVal-dPro-Arg-dLeu-dThr<br>A   A   A   A   A   Y    Y    A   Y    Y | YA(i,i+3)<br>YAA(i,i+3/i+1,i+4)<br>AAA(i,i+3/i,i+4) | Glu2-Arg6(NH)<br>Glu2-Arg6 |
| design 10.2 | Glu-dVal-Asp-Pro-dGlu-dHis-dPro-Asn-dAla-dPro<br>A   X    B   B   X    Y    Y    A   Y    Y | YA(i,i+3)<br>BX(i,i+3)<br>YAX(i,i+3/i,i+4) | Asp3-Asn8(NH) |

TABLE 1-continued

Different structural features observed for experimentally verified designs. (from top to bottom SEQ ID NOs: 230, 231, 232, 233, 32, 234, 235, 236, and 237)

| name | critical residues | additional important residues |
|---|---|---|
| design 7.1 | dPro4 | |
| design 7.2 | dPro5, dPro7 | |
| design 7.3 | Pro3 | dThr6:polar interaction with dPro4 |
| design 7.4 | Asp5 | Arg7:hbond to Asp5 |
| design 8.1 | Asp2, Pro3, dPro5 | |
| design 8.2 | most | S2 symmetric backbone |
| design 9.1 | dPro5, Pro9 | Pro9 stabilizes a bulge Tyr7 packs against Pro6 |
| design 10.1 | | long range bb to bb hydrogen bond Ala2, dVal6, dLeu9: hydrophobic packing |
| design 10.2 | | dVal2, dAla8: hydrophobic interaction |

As the macrocycle length increases (9 and 10 residues, FIG. 2), so does the entropic cost of folding, and more hydrogen bonds in increasingly diverse patterns are required to stabilize the peptide in the folded state. Three of six experimentally characterized designs had structures close to computational models, one was disordered, and two had well dispersed spectra but the NOE data did not uniquely define the structures. Design 9.1 contains a YAA i,i+3/i,i+4 building block similar to those in the 7-residue macrocycles in which dPro5 plays a critical role (as in the L-Pro/D-Pro in design 7.3, the second proline plays a less critical role). The structure is expanded by insertion of a kink stabilized by Pro9; the remainder of the structure is completed by a tight AAA i,i+3/i,i+4 turn. Design 10.1 contains a 5 residue distorted helix terminated by the critical dPro7. On one face the structurally critical Glu2 in the middle of the helix makes a long range sidechain-backbone hydrogen bond to Arg8, and on the other, Ala3, dVal6, and dLeu9 form a non-polar cluster. Design 10.2 contains BX, YA and the rare YAA building blocks each beginning with a proline residue; of these, Pro4 in the BX motif is the most critical. As with 10.1, the building blocks are held together by nonpolar interactions (between dVal2 and dAla8) on one face, and a long-range sidechain-backbone hydrogen bond (from Asp3 to Asn8) on the other; both dVal2 and Asp3 are critical for specifying the structure.

The entropic cost of folding continues to increase with increasing number of residues, and for 11-14 residue macrocycles, additional crosslinks to form bicyclic structures were required to obtain single states amenable to NMR structure determination. We solved the structures of 3 such designs (FIG. 2, row IV) that feature long-range backbone-backbone hydrogen bonds. Design 11_SS has a i,i+1/i+1,i+4 building block (this motif connects residue 1 and one residues after that with a hydrogen bond (I,i+1), and also connects the residue after residue 1 (i+1) with and fourth residue after that (i+4) with a turn) with a critical proline in the first position preceded by a cysteine that forms a critical disulfide to a cysteine preceding a YA turn. Design 12_SS has a rare BXAX i,i+4/i,i+5 turn (this motif connects residue 1 and four residues after that with a hydrogen bond (I,i+4) and connects residue 1 and fifth residue after that (i+5) with a hydrogen bond (I,i+5)), which exhibits higher flexibility in NMR structure, and a disulfide between backbone hydrogen bonding residues. The more compact and complex 14_SS design has a network of interleaved local and non-local backbone hydrogen bonds (22), and a D-Cys to L-Cys disulfide bond.

The wide variety of shapes spanned by our macrocycle designs, together with their high stability and high predicted tolerance for sequence mutations, makes them attractive starting points for developing new therapeutics. One approach to inhibitor design is scaffolding loops at binding interfaces in the PDB; such scaffolding can increase binding affinity by pre-organizing the loops in the binding-competent conformation, enable additional interactions with the target, and improve cell permeability and oral bioavailability (23). We found that 907 of the 1017 "hot loops" identified at protein-protein interfaces by Kritzer and coworkers (24) could be scaffolded by one or more of our designs.

The finding that 70% of the experimentally-tested 7- to 10-residue macrocycle designs adopt single unique structures close to the computationally-designed models suggests that most of the 200+ new macrocycle designs with high computed Boltzmann weights fold as designed, increasing the known repertoire of possible macrocycle structures by more than two orders of magnitude. Our results demonstrate that the principles and energy functions developed in recent years to design proteins have quite broad applicability, transferring over to much smaller systems even though (1) the factors dominating the folding of proteins (for example, the hydrophobic effect) differ considerably from those that stabilize conformations of small peptide macrocycles (local hydrogen bonding patterns and intrinsic conformational preferences of amino acid building-blocks), and (2) all designed proteins to-date contain regular α-helix or β-sheet structures, while small peptide macrocycles lack these and instead contain a wide range of local structures some of which are rarely or never observed in proteins.

There are two clear paths forward for engineering new macrocyclic therapeutics by exploiting the rigidity and stability of the designs together with the freedom to choose the identities of the non-structure specifying positions. The first is experimental: libraries can be constructed in which at each position all residues compatible with the structure are allowed (identified as described above using large-scale energy landscape calculations), and screened for target binding using current library selection methodologies. The second is computational: each macrocycle can be docked against the target (using for example rigid body docking or "hot loop" superposition), and the interface residues designed to maximize binding affinity. Unnatural amino acids can be incorporated in either approach, but the second has the advantage that new functionalities—such as known active site binding groups—can be strategically placed to maximize binding affinity. Beyond binding, the control over geometry and chemistry provided by our approach should contribute to understanding the structural correlates of membrane permeability and other desirable pharmacological properties.

Methods

Backbone Conformational Sampling

Conformations of 7- to 14-residue polyglycine backbones were sampled using the previously-described Rosetta™ simple_cycpep_prediction application (15), with key modifications. Unlike the Rosetta™ ab initio method used for protein structure prediction (25), simple_cycpep_predict does not make use of fragments of proteins of known structure, since such fragments poorly cover the conformational space accessible to chains of mixtures of L- and D-amino acids. Instead, it uses an efficient kinematic closure-based algorithm (17, 26) that samples only closed conformations to limit the search space. Briefly, the sampling process consisted of the following steps: first, a linear chain of glycine residues was constructed, one residue of which was selected randomly to be the "anchor" residue for subsequent loop closure steps. The N- and C-terminal residues were excluded from being the anchor residue. This residue's mainchain φ and Ψ dihedral values were drawn randomly from a flat, symmetric Ramachandran distribution based on the glycine Ramachandran map. Second, a bond was declared between the nitrogen of the N-terminal residue and the carbonyl carbon of the C-terminal residue, and the Rosetta generalized kinematic closure (GenKIC) module was invoked to close the loop consisting of all residues but the anchor residue. During this process, the φ and Ψ dihedral values of all but three residues in the loop were randomized, biased by the same flat, symmetric distribution used to randomize the anchor residue, and the φ and Ψ dihedral values for the remaining three residues were determined algebraically to ensure loop closure with ideal peptide bond geometry at the cutpoint (the bond between the first and last residues). In preliminary design calculations, we found that unique low-energy structures with energy gaps greater than $\sim 10$ $k_B T$ ($\sim 6$ kcal/mol) could only be obtained for macrocycles containing at least N/3 backbone hydrogen bonds; therefore, in subsequent sampling calculations, of the many closure solutions found, those with mainchain hydrogen bond counts below the threshold value were discarded. Third, the cyclic backbone was relaxed with the Rosetta FastRelax™ protocol (27) using the all-atom Rosetta™ energy function "ref2015"(28, 29), with the rama_prepro and p_aa_pp mainchain potentials made symmetric, as described previously (15). Up to $10^8$ samples were attempted, not all of which yielded closed solutions with the desired minimum number of hydrogen bonds.

Sampling was carried out on the "Mira" Blue Gene/Q supercomputer (Argonne labs) or Amazon Web Service (AWS). For efficiency, a new multi-level hierarchical job distribution and data reduction scheme was implemented for use on massively parallel architecture. In performance benchmarks, this yielded linear performance scaling up to at least 250,000 CPUs.

Energy-Based Clustering and Data Reduction

The sampling described above yields up to millions of backbones, making the problem of identifying repeatedly-sampled conformations a difficult problem in data reduction. While many algorithms for clustering large datasets have been developed (30-32), this particular problem has an interesting feature: Rosetta's energy calculations can be used to establish a rank order for the degree to which elements in the dataset are "interesting", providing a useful means of selecting cluster centers without performing a prohibitively expensive all-to-all RMSD calculation.

We developed a simple energy-based clustering algorithm for this problem: first, the energy of each input structure is scored using the Rosetta™ all-atom energy function (ref2015), and minimal backbone information for every structure is stored in an unclustered pool. Second, the lowest-energy structure in the unclustered pool is selected as the center of the first cluster. This structure is moved from the unclustered pool into the first cluster, and the backbone RMSD between this structure and every circular permutation of every structure remaining in the unclustered pool is calculated. Those structures for which at least one circular permutation lies within a threshold RMSD from the current cluster center are also removed from the unclustered pool and added to the new cluster. For our purposes, we typically used an RMSD threshold of 1.25 Å. Third, the lowest-energy structure remaining in the unclustered pool is selected as the center of the next cluster, and the second step is repeated. This process continues for subsequent clusters until no structures remain in the unclustered pool. Note that, unlike Voronoi clustering schemes, this "cookie-cutter" approach deliberately gives precedence to lower-energy clusters. Although simple, we found that this approach worked well for our large datasets, yielding lower-energy clusters that were particularly easy to stabilize with suitable amino acid sequences.

Torsion Bin-Based Clustering

We developed a custom PyRosetta™ Python script for re-clustering the cluster centers from the previous, RMSD-based clustering step. Briefly, this script assigns a torsion bin string to each input structure, sorting all circular permutations in both chiralities of the bin string alphabetically and selecting the first in order to allow structures with different circular permutations to be compared easily. A string representing a hydrogen bonding pattern is also assigned to each input structure, circularly permuted to match the circular permutation of the torsion bin string. The structure is then assigned to a cluster with the same torsion bin string and hydrogen bonding pattern, or, if no such cluster has yet been encountered, a new cluster is created and the structure is assigned to that new cluster. The process is repeated until all input structures have been assigned to clusters.

Computational Sequence Design

The Rosetta FastDesign™ module was used for sequence design. FastDesign™ performs alternating rounds of side-chain identity and rotamer optimization (using the Rosetta Packer™ module) and torsion-space energy minimization (using the Rosetta Minimizer™ module), with the repulsive term of the Rosetta™ energy function, fa_rep, ramped from 2% of its normal value to 100% of its normal value from round to round.

FastDesign™ seeks to minimize the energy of a designed structure. However, there were additional requirements that we wished to impose during the design process. Some such requirements were intended to limit the conformational flexibility of the designs produced, and to maximize the chances of the designed structure representing a unique low-energy conformation. To this end, we wished to require a minimum L- or D-proline content, for example. Other requirements were practical needs for synthesis (e.g. the need for at least one L-aspartate or L-glutamate in the sequence to allow resin tethering during cyclization), or for characterization (e.g. the need for at least one positively-charged residue to facilitate mass spectrometry).

To this end, we implemented a non-pairwise-decomposable term, called aa_composition, which allowed users to define a nonlinearly-ramping penalty for deviation from a desired amino acid composition to guide the Packer™ to find sequences with desired compositions. This allowed us to require a minimum proline count, and at least one L-aspartate or L-glutamate and one positively charged residue per design.

We also implemented two new residue selectors, called the PhiSelector™ and BinSelector™, to provide additional control over the Packer™. We used these to require that the Packer™ consider only L-amino acid residues at positions with a mainchain φ value less than zero, and only D-amino acid residues at positions with a mainchain φ value greater than zero.

During early design runs, we found that Rosetta™'s normally pairwise-decomposable scoring function would erroneously favor structures in which more than two hydrogen bond donors made bonds to a single acceptor. Since it is difficult to change the hydrogen bonding architecture to give favorable scores to a maximum of two donors binding to an oxygen acceptor (since such scoring would necessarily be non-pairwise-decomposable), we instead implemented a filter to discard designs with this pathology.

Computational Validation: Energy Landscape Analysis of Designed Macrocycles and Their Mutants For each torsion bin string and hydrogen bonding pattern, the lowest-energy sequence designed was picked as a representative of that cluster. A subset of such low-energy structures (from 44% of all designs for length 7 to 3% of all designs for length 10) was subjected to a final round of computational validation using the simple_cycpep_predict application, as described previously (15). As for the sampling of polyglycine conformations, large numbers of backbone conformations were sampled for each sequence tested, but this time, the sampling was biased based on the Ramachandran map of each amino acid residue in the sequence. Each sample was subjected to full side-chain rotamer optimization and energy minimization using the Rosetta FastRelax™ protocol (27). The "foldability" of each macrocycle was evaluated based on the estimated fractional occupancy of the native state (a value that we call $P_{Near}$), and on the energy gap between the native structures and other low energy models, as reported previously (15). A $P_{Near}$ value of >0.9 and energy gap of <−0.1 was selected as the basic threshold for acceptance. Additionally, the plot of energy vs. RMSD was then visually inspected.

For a subset of macrocycles, large-scale landscape analysis was performed. Each residue in the initial sequence was systematically mutated to the other 18 amino acid residues of the same chirality, and to alanine with mirror chirality, in the input sequences provided to the simple_cycpep_predict application. These large scale computational analyses of the energy landscape was performed using the Berkeley Open Infrastructure for Network Computing (BOINC) as part of the Rosetta@Home™ project, mostly using volunteer cellular telephones as the computing hardware (though some earlier predictions were carried out using volunteer desktop computers, or using the Argonne "Mira" Blue Gene/Q system used for poly-Gly conformational sampling).

Scrambled sequences were generated by randomly assigning residues to different positions in the structure.

After generation of results, site-saturation mutagenesis plots were generated based on $P_{Near}$ values (see equation below for $P_{Near}$) for each structure, with λ set to 1 Å and a value of $k_B T$ of 0.62 kcal/mol (equivalent to 37° C.). For two of the macrocycles, different combinations of λ and $k_B T$ (0.5, 0.75, 1, 1.5 for 1 and 0.5, 0.75, 1, 2 for $k_B T$) were tested and the value with more dynamic range (i.e. values that showed the difference between a high-quality vs. low-quality energy funnel best) were selected. Double mutants were generated and analyzed using similar methods described above.

Equation 1: Definition of $P_{Near}$, a measure of the quality of an energy function. $P_{near}$ approximates the Boltzmann-weighted probability of finding the structure in a conformation near the native conformation.

$$P_{near} = \frac{\sum_{i=1}^{N} \exp\left(-\frac{rmsd_i^2}{\lambda^2}\right)\exp\left(-\frac{E_i}{k_B T}\right)}{\sum_{i=1}^{N} \exp\left(-\frac{E_j}{k_B T}\right)}$$

Turn Type Analysis and Measurement of RMSD to Hot Loops

We defined a turn as a semi-independent part of a macrocycle structure that is connected internally through backbone-to-backbone hydrogen bonds, but which lacks hydrogen bonds to other parts of the structure. For each structure, different turn types were defined by their torsion bin strings and hydrogen bond patterns. Similar analysis was performed on a subset of structures from the PDB, and the frequencies were then calculated and compared. The redundancy of the PDB subset was reduced to 30%—that is, no two PDB chains in the set had more than 30% sequence identity.

From all the hot loops generated by Kritzer and coworkers (24), those that contained continuous stretches of amino acids were selected. Each loop, and small truncations of it (one residue shorter from each side) were then compared to a library of macrocycles that passed computational consistency check. For every motif and scaffold, a matrix of pairwise distances between C-alpha atoms and a vector of dihedral angles for every four consecutive C-alpha atoms was computed. For every possible alignment of linear motif to cyclic scaffold, Root-Mean-Square of the differences of both the distance matrices (distance RMS) and the dihedral vectors (dihedral RMS) is reported. Macrocycles that at least in one position had a distance RMSD of less than 1 Å and a dihedral RMSD of less than 10 degrees (i.e. contained a portion matching the motif backbone) were considered to be plausible stabilizing scaffolds for the given motif. A complete list of these hot loops and the results are available as a supplementary file.

Synthesis, Purification, and Mass Spectrometry of Macrocycles

All peptides were synthesized using standard Fmoc solid phase peptide synthesis (SPPS) on preloaded and sidechain-linked Fmoc-Asp (Wang resin LL)-ODmab or Fmoc-Glu (Wang resin LL)-ODmab resin. Linear, protected peptides were built on a CEM Liberty Blue Peptide Synthesizer with microwave heating at coupling and deprotection steps. After the final Fmoc deprotection, the resin was treated with 2% (v/v) hydrazine monohydrate in dimethylformamide (DMF) to remove the C-terminal Dmab protecting group; the N- and C-termini were then joined on-resin by a coupling reaction. A cleavage cocktail of TFA:Water:TIPS:DODT (92.5:2.5:2.5:2.5) used for global deprotection of side-chains and to cleave the peptide from the resin. After the removal of residual TFA by evaporation, peptides were ether precipitated and further purified using RP-HPLC.

Crude peptides were purified using an Agilent Infinity Preparative HPLC with an Agilent Zorbax™ SB-C18 column (9.4 mm×250 mm). A linear gradient of 1%/min for Solvent B (ACN with 0.1% TFA) and flow rate of 5 ml/min was used for purification to collect fractions with pure peptides. Mass and purity of peptides were confirmed using electrospray ionization mass spectrometry (ESI-MS) on a Thermo Scientific TSQ Quantum Access mass spectrometer.

For disulfide-stapled peptides, cyclic reduced peptides were air-oxidized in 0.1 M ammonium bicarbonate buffer (pH 8.3) for 48 hours, and purified again using RP-HPLC. Some of the disulfide-containing peptides were synthesized with Fmoc-Cys(Acm)-OH at the cysteine positions. Following synthesis and cyclization, the resin was treated with 8 eqs. of iodine in 4:1 DMF:methanol overnight to remove the Acm protecting groups and facilitate disulfide bond formation. After iodine treatment, the resin was washed with 2% w/v ascorbic acid in DMF, rinsed with dichloromethane (DCM) and cleaved and purified as normal.

Nuclear Magnetic Resonance (NMR) Spectroscopy Studies of the Designed Macrocycles Each peptide macrocycle was dissolved at concentrations of ~5 mg/mL at a pH between 3.0 and 5.5 in 10% $D_2O$, with up to 5% glycerol-$d_8$ added. All NMR data were collected on a DRX 500 MHz, an Avance™ III 600 MHz, or an Avance™ III 800 MHz spectrometer, equipped with TCI cryoprobe and triple-axis gradient (Bruker). Unless otherwise noted, all NMR data were collected at 5° C. and 25° C. using pulse sequences with excitation sculpting water suppression. Data were processed with TOPSPIN™ v. 3.5 (Bruker) or NMRPIPE™ (34) and visualized with Sparky. Initial screening of designed cyclic peptides for discrete structure involved recording 1D spectra at 25° C. and selecting peptides with sharp, and well dispersed backbone amide resonances. The small size of the peptides (<=14 residues) selected for structural analysis allowed for complete proton backbone and side chain resonance assignment using 2D [$^1H$, $^1H$] TOCSY including many stereospecific assignments. To facilitate quantitative evaluation of internuclear distances, sample temperatures were dropped to 5° C. and both 2D [$^1H$, $^1H$]-ROESY with a 200 ms mixing time and 2D [$^1H$, $^1H$] NOESY spectra were collected using mixing times of 100 ms and 500 ms. For designs 8.1 and 14_SS a full NOESY buildup curve (50-75 ms mixing time) was collected to ensure linear behavior of the glycerol containing samples of small peptides (fig. S28). Because it is currently not economical to prepare uniformly $^{13}C$ and $^{15}N$-labelled peptides using solid phase methods, and because natural abundance experiments are resource-intensive, only a set of $^{15}N$ assignments were measured using natural abundance 2D [$^{15}N$, $^1H$] SOFAST HMQC for designs 7.1. 7.2, 8.1, 8.2, 12_SS, 14_SS. For longer peptide designs or designs with clear overlap in the 2D [$^1H$, $^1H$] TOCSY we also collected natural abundance 2D [$^{13}C$, $^1H$] HMQC.

Nuclear Overhauser Effect (NOE) Constraint Consistency Check

To evaluate whether NOE constraints alone can predict the designed structure, we first used Rosetta to relax 5 macrocycles from the Protein Data Bank (PDB) and Cambridge Structural Database (CSD) that shared the same criteria as our peptides (4ME6 from the PDB and CUQYUI, DUYTIA, MANGO, and UZUKUW from the CSD); this was repeated 20 times. Based on the observed distribution of energies after relaxation, we set the following filters for the score terms below and selected structures that passed these filters from our previous landscape analysis:
omega=1, fa_rep=10, fa_intra_rep=0.5, pro_close=5, rama_prepro=3

Each structure was then rescored, using Rosetta, based solely on how well it satisfied the NOE constraints and the scores vs. RMSD to design were plotted.

NMR Structure Determination of Designed Macrocycles

A set of 200 structures were calculated for well-behaved designs with the Xplor-NIH software package using torsion angle dynamics and simulated annealing. Initial folding was conducted from a single starting template of randomized torsional angles for the cyclic peptide after patching L- or D-stereoisomers. Distance restraints were derived from NOE intensities at 100 and 500 ms mixing times in 2D [$^1$H, $^1$H] NOESY spectra recorded at 500 or 800 MHz and were sorted into Strong (2.5 0.7 0.7), Medium (3.5 1.5 1.5) and Weak (4.5 2.0 2.0) bins based on relative peak intensities to aromatic resonance signals. A soft square potential was used for NOE restraints for initial folding and convergence was established when there were no NOE violations greater than 0.5 Å of the calculated structures.

After initial folding, hydrogen-bonding restraints were inferred from proximal atoms, identified by cross-strand or nearest neighbor amide NOE cross peaks in the 2D [$^1$H-$^1$H] NOESY or monitoring slow exchanging protons with 1D $^1$H CLEANER-PM pulse sequences (mixing time 0-500 ms). After backbone hydrogen bonding was established, structures were re-calculated as described incorporating hydrogen bonds as NOE restraints using a biharmonic potential. Throughout folding and refinement, only NOE and van der Waals terms were active during structure calculation. Due to lack of uniform labeling and peak overlap we were not able to make clear predictions of backbone dihedral angle restraints or coupling constants. The torsional database constraints were also left unrestrained due to lack of sufficient information for handling D-amino acids. To refine the structures based on NMR experiments, we launched MD simulations with NOE constraints. In particular, for each structure, a simulated annealing from 350K to 310K followed by a 10-ns production run was performed (35). For each atom pair measured by NOE, a distance restraint (k=1000 kJ mol$^{-1}$ nm$^{-1}$) was applied throughout the simulation. The 20 conformations with the lowest total energy were selected for further analysis.

MD Simulation of Designed Macrocycles

Molecular Dynamics simulations were performed using GROMACS™ 2016.1(36, 37) with the Amber™ 99SB-ILDN forcefield (38). Each peptide was solvated in a dodecahedron box of explicit TIP3P waters(39) and neutralized with either sodium or chloride ions. The solvated systems were energy-minimized using the steepest descent minimization method. Next, the system was equilibrated for 1 ns under the NPT ensemble with position restraints (1000 kJ mol$^{-1}$ nm$^{-1}$) applied on all the heavy atoms of the peptide. During this equilibration, pressure coupling to 1 atm was performed with the Berendsen barostat (40), and temperature coupling to 310 K using the velocity-rescaling thermostat (41). From each equilibrated system, 10 simulations of 100 ns were performed in the NVT ensemble. The systems were simulated using periodic boundary conditions. A cutoff at 10 Å was used for van der Waals and short-range electrostatic interactions. The Particle-Mesh Ewald (PME) summation method was used for the long-range electrostatic interactions (42). The Verlet cut-off scheme was used (43). All chemical bonds were constrained using the LINCS algorithm (44). The integration time-step was 2 fs, and simulations were analyzed using GROMACS tools. We calculated the root-mean-square deviation (RMSD) of the position of the $C_\alpha$ atoms of the peptides, compared to the initial conformation, using gmx rms. The peptides were aligned to the $C_\alpha$ of the initial conformation. The Ramachandran plots were calculated using gmx chi, and plotted using the Matplotlib histogram2d function.

For two of the structures, design 8.1 and 10.1, we also performed our analysis for the mirrored structure of the designs to make sure that our calculations are not energetically biased against L- or D-amino acids. As shown in fig. S29, the results are comparable; thus, we only performed simulations of the designed structure (and not its mirror image) for the rest of the macrocycles.

For designs 7.3 and 7.4, we performed long (>1 µs) molecular dynamics simulations to analyze the dynamics of folding and different conformations explored by the macrocycles. The Markov state model that captures movement of the macrocycle was generated by MSM builder, and the dynamics of movement were described using a time-structure independent component analysis (t1CA) model(44-47).

Ion Mobility Spectrometry Analysis

The single-site mutant libraries of design 7.1 were synthesized with a process similar to that described above with an additional step. For the residues for which the mutation was made (dPro4 or Thr5), the resin was removed from the synthesizer and split into 6 pools. Each pool had its respective amino acid coupled individually using the synthesizer (D-Pro, D-Ser, D-Asn, D-Asp, D-Met, D-Arg for position 4 and Thr, Ser, Leu, Gln, Glu, Trp for position 5). After all pools of resin were loaded with the desired amino acid they were recombined and the remaining amino acids in the sequence were coupled as normal. Cleavage of the resin was performed using the same cleavage cocktail described above. All expected species were confirmed by mass spectrometry.

All samples were prepared in 50% aqueous methanol acidified with 0.1% formic acid. The solutions were infused at an infusion rate of 300 nL/min and electrosprayed in the positive mode using an etched emitter (20 mm i.d.). The formed ions were transmitted through a heated inlet capillary (130° C.) into a high-resolution Structures for Lossless Ion Manipulations Ion Mobility Mass Spectrometer (SLIM IM-MS) platform for high resolution ion mobility spectrometry (21). Ions were accumulated in an ion funnel trap (48) for 2 ms and then released to SLIM IM-MS. The SLIM module was similar to that of the SLIM serpentine design previously reported (49, 50), but has a path length of 15.9 m that allows for multiple passes through the serpentine path for higher ion mobility spectrometry resolution. The SLIM module was integrated with an Agilent 6224 TOF MS equipped with a 1.5 m extended flight tube via a rear ion funnel and RF-only quadrupole. All SLIM separations were performed at ~2.5 Torr $N_2$ with the following parameters: wave speed of 160 m/s, wave amplitudes of 40 V, guard electrode voltage of 6 V, and RF frequency of 1.0 MHz and amplitude of 380 $V_{p-p}$. Data were acquired on an 8-bit ADC (analog-to-digital converter) using a control software developed in-house.

Protease Assay

Protease assay was performed using PRONASE® Protease derived from *Streptomyces griseus* from EMD Millipore (product# 53702), 0.2 µmole of each peptide tested was added to 200 µl of 50 mM ammonium acetate buffer, pH 8, supplemented with 0.01 M calcium acetate. 5 µl of this starting material was mixed with µl TFA and kept as the time 0 sample. To this mixture we added 2 µl of 2 mg/ml protease mix stock (prepared by dissolving in water) and incubated at 37° C. At different time points, 5 µl of the reaction mixture was taken out and quenched by addition of 5 µl TFA. To track protease cleavage, each sample was analyzed by LC/MS (Thermo Scientific Accela HPLC system connected to Thermo Scientific TSQ Quantum Access mass spectrometer) using an Agilent ZORBAX™ StableBond™ 300 C18, 4.6×150 mm, 5 μm as the chromatography column.

REFERENCES

1. E. M. Driggers, S. P. Hale, J. Lee, N. K. Terrett, The exploration of macrocycles for drug discovery—an under-exploited structural class. *Nat. Rev. Drug Discov.* 7, 608-624 (2008).

2. P. Thapa, M. J. Espiritu, C. Cabalteja, J.-P. Bingham, The Emergence of Cyclic Peptides: The Potential of Bioengineered Peptide Drugs. *Int. J. Pept. Res. Ther.* 20, 545-551 (2014).

3. K. Fosgerau, T. Hoffmann, Peptide therapeutics: current status and future directions. *Drug Discov. Today.* 20, 122-128 (2015).

4. D. J. Craik, D. P. Fairlie, S. Liras, D. Price, The future of peptide-based drugs. *Chem. Biol. Drug Des.* 81, 136-147 (2013).

5. B. P. Gray, K. C. Brown, Combinatorial peptide libraries: mining for cell-binding peptides. *Chem. Rev.* 114, 1020-1081 (2014).

6. D. Marasco, G. Perretta, M. Sabatella, M. Ruvo, Past and future perspectives of synthetic peptide libraries. *Curr. Protein Pept. Sci.* 9, 447-467 (2008).

7. R. Liu, X. Li, W. Xiao, K. S. Lam, Tumor-targeting peptides from combinatorial libraries. *Adv. Drug Deliv. Rev.* 110-111, 13-37 (2017).

8. R. Obexer, L. J. Walport, H. Suga, Exploring sequence space: harnessing chemical and biological diversity towards new peptide leads. *Curr. Opin. Chem. Biol.* 38, 52-61 (2017).

9. T. Passioura, H. Suga, A RaPID way to discover nonstandard macrocyclic peptide modulators of drug targets. *Chem. Commun.* 53, 1931-1940 (2017).

10. P.-S. Huang et al., High thermodynamic stability of parametrically designed helical bundles. *Science.* 346, 481-485 (2014).

11. P.-S. Huang et al., De novo design of a four-fold symmetric TIM-barrel protein with atomic-level accuracy. *Nat. Chem. Biol.* 12, 29-34 (2015).

12. S. E. Boyken et al., De novo design of protein homo-oligomers with modular hydrogen-bond network-mediated specificity. *Science.* 352, 680-687 (2016).

13. E. Marcos et al., Principles for designing proteins with cavities formed by curved β sheets. *Science.* 355, 201-206 (2017).

14. P.-S. Huang, S. E. Boyken, D. Baker, The coming of age of de novo protein design. *Nature.* 537, 320-327 (2016).

15. G. Bhardwaj et al., Accurate de novo design of hyperstable constrained peptides. *Nature.* 538, 329-335 (2016).

16. E. A. Coutsias, C. Seok, M. P. Jacobson, K. A. Dill, A kinematic view of loop closure. *J. Comput. Chem.* 25, 510-528 (2004).

17. D. J. Mandell, E. A. Coutsias, T. Kortemme, Sub-angstrom accuracy in protein loop reconstruction by robotics-inspired conformational sampling. *Nat. Methods.* 6, 551-552 (2009).

18. C. D. Schwieters, J. J. Kuszewski, G. M. Clore, Using Xplor-NIH for NMR molecular structure determination. *Prog. Nucl. Magn. Reson. Spectrosc.* 48, 47-62 (2006).

19. C. D. Schwieters, J. J. Kuszewski, N. Tjandra, G. M. Clore, The Xplor-NIH NMR molecular structure determination package. *J. Magn. Reson.* 160, 65-73 (2003).

20. J. Rizo, L. M. Gierasch, Constrained Peptides: Models of Bioactive Peptides and Protein Substructures. *Annu. Rev. Biochem.* 61, 387-416 (1992).

21. Y. M. Ibrahim et al., New frontiers for mass spectrometry based upon structures for lossless ion manipulations. *Analyst.* 142, 1010-1021 (2017).

22. E. G. Hutchinson, J. M. Thornton, A revised set of potentials for β-turn formation in proteins. *Protein Sci.* 3, 2207-2216 (1994).

23. D. S. Nielsen et al., Orally Absorbed Cyclic Peptides. *Chem. Rev.* 117, 8094-8128 (2017).

24. J. Gavenonis, B. A. Sheneman, T. R. Siegert, M. R. Eshelman, J A Kritzer, Comprehensive analysis of loops at protein-protein interfaces for macrocycle design. *Nat. Chem. Biol.* 10, 716-722 (2014).

25. P. Bradley, K. M. S. Misura, D. Baker, Toward high-resolution de novo structure prediction for small proteins. *Science.* 309, 1868-1871 (2005).

26. E. A. Coutsias, C. Seok, K. A. Dill, Using quaternions to calculate RMSD. *J. Comput. Chem.* 25, 1849-1857 (2004).

27. F. Khatib et al., Algorithm discovery by protein folding game players. *Proc. Natl. Acad. Sci. U.S.A.* 108, 18949-18953 (2011).

28. R. F. Alford et al., The Rosetta All-Atom Energy Function for Macromolecular Modeling and Design. *J. Chem. Theory Comput.* 13, 3031-3048 (2017).

29. H. Park et al., Simultaneous Optimization of Biomolecular Energy Functions on Features from Small Molecules and Macromolecules. *J. Chem. Theory Comput.* 12, 6201-6212 (2016).

30. S. C. Li, Y. K. Ng, Calibur: a tool for clustering large numbers of protein decoys. *BMC Bioinformatics.* 11, 25 (2010).

31. B. North, A. Lehmann, R L Dunbrack Jr, A new clustering of antibody CDR loop conformations. *J. Mol. Biol.* 406, 228-256 (2011).

32. J. J. Gray et al., Protein-protein docking with simultaneous optimization of rigid-body displacement and side-chain conformations. *J. Mol. Biol.* 331, 281-299 (2003).

33. S. J. Fleishman et al., RosettaScripts: a scripting language interface to the Rosetta macromolecular modeling suite. *PLoS One.* 6, e20161 (2011).

34. F. Delaglio et al., NMRPipe: a multidimensional spectral processing system based on UNIX pipes. *J. Biomol. NMR.* 6, 277-293 (1995).

35. O. F. Lange et al., Recognition dynamics up to microseconds revealed from an RDC-derived ubiquitin ensemble in solution. *Science.* 320, 1471-1475 (2008).

36. M. J. Abraham et al., GROMACS: High performance molecular simulations through multi-level parallelism from laptops to supercomputers. *SoftwareX.* 1-2, 19-25 (2015/9).

37. S. Páll, M. J. Abraham, C. Kutzner, B. Hess, E. Lindahl, in *Solving Software Challenges for Exascale* (Springer, Cham, 2014), pp. 3-27.

38. K. Lindorff-Larsen et al., Improved side-chain torsion potentials for the Amber ff99SB protein force field. *Proteins.* 78, 1950-1958 (2010).

39. J. Leszczynski, M. K. Shukla, *Practical Aspects of Computational Chemistry: Methods, Concepts and Applications* (Springer Science & Business Media, 2009).

40. H. J. C. Berendsen, J. P. M. Postma, W. F. van Gunsteren, A. DiNola, J. R. Haak, Molecular dynamics with coupling to an external bath. *J. Chem. Phys.* 81, 3684-3690 (1984).

41. G. Bussi, D. Donadio, M. Parrinello, Canonical sampling through velocity rescaling. *J. Chem. Phys.* 126, 014101 (2007).

42. U. Essmann et al., A smooth particle mesh Ewald method. *J. Chem. Phys.* 103, 8577-8593 (1995).

43. S. Páll, B. Hess, A flexible algorithm for calculating pair interactions on SIMD architectures. *Comput. Phys. Commun.* 184, 2641-2650 (2013).

44. B. Hess, H. Bekker, H. J. C. Berendsen, J. G. E. M. Fraaije, LINCS: A linear constraint solver for molecular simulations. *J. Comput. Chem.* 18, 1463-1472 (1997).

45. C. R. Schwantes, V. S. Pande, Improvements in Markov State Model Construction Reveal Many Non-Native Interactions in the Folding of NTL9. *J. Chem. Theory Comput.* 9, 2000-2009 (2013).

46. B. Cronkite-Ratcliff, V. Pande, MSMExplorer: visualizing Markov state models for biomolecule folding simulations. *Bioinformatics.* 29, 950-952 (2013).

47. G. Pérez-Hernández, F. Paul, T. Giorgino, G. De Fabritiis, F. Noé, Identification of slow molecular order parameters for Markov model construction. *J. Chem. Phys.* 139, 015102 (2013).

48. Y. Naritomi, S. Fuchigami, Slow dynamics in protein fluctuations revealed by time-structure based independent component analysis: the case of domain motions. *J. Chem. Phys.* 134, 065101 (2011).

49. Y. Ibrahim, M. E. Belov, A. V. Tolmachev, D. C. Prior, R. D. Smith, Ion funnel trap interface for orthogonal time-of-flight mass spectrometry. *Anal. Chem.* 79, 7845-7852 (2007).

50. L. Deng et al., Ultra-High Resolution Ion Mobility Separations Utilizing Traveling Waves in a 13 m Serpentine Path Length Structures for Lossless Ion Manipulations Module. *Anal. Chem.* 88, 8957-8964 (2016).

We claim:

1. A macrocyclic polypeptide comprising the amino acid sequence of any one of SEQ ID NO: 1-237 or a mirror image thereof, wherein the polypeptide is N-terminus to C-terminus cyclized.

2. The macrocyclic polypeptide of claim 1, wherein the macrocyclic polypeptide is between 7 and 14 amino acid residues in length, or between 7 and 10 amino acid residues in length.

3. A polypeptide library, comprising two or more different polypeptides comprising the amino acid sequence of any one of SEQ ID NO: 1-237 or a mirror image thereof, wherein the polypeptides are N-terminus to C-terminus cyclized.

4. The polypeptide library of claim 3, comprising ten or more different polypeptides comprising the amino acid sequence of any one of SEQ ID NO: 1-237 or a mirror image thereof.

5. The polypeptide library of claim 4, comprising fifty or more different polypeptides comprising the amino acid sequence of any one of SEQ ID NO: 1-237 or a mirror image thereof.

6. The polypeptide library of claim 5, comprising two hundred or more different polypeptides comprising the amino acid sequence of any one of SEQ ID NO: 1-237 or a mirror image thereof.

7. The macrocyclic polypeptide of claim 1, consisting of the amino acid sequence of any one of SEQ ID NO: 1-237 or a mirror image thereof.

8. The polypeptide library of claim 3, comprising two or more polypeptides consisting of the amino acid sequence of any one of SEQ ID NO: 1-237 or a mirror image thereof, wherein the polypeptides are N-terminus to C-terminus cyclized.

9. The macrocyclic polypeptide of claim 1, wherein the macrocyclic polypeptide comprises the amino acid sequence of SEQ ID NO:234.

10. The macrocyclic polypeptide of claim 1, wherein the macrocyclic polypeptide consists of the amino acid sequence of SEQ ID NO:234.

* * * * *

SEQUENCE LISTING

```
<160> NUMBER OF SEQ ID NOS: 237

<210> SEQ ID NO 1
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(6)
<223> OTHER INFORMATION: D-chirality

<400> SEQUENCE: 1

His Pro Asp Gln Ser Glu Pro
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (3)..(3)
<223> OTHER INFORMATION: D-chirality

<400> SEQUENCE: 2

Arg Lys Pro Pro Asp Glu Asp
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
```

```
<222> LOCATION: (7)..(7)
<223> OTHER INFORMATION: D-chirality

<400> SEQUENCE: 3

Pro Asn Ser Glu Pro Asn Asn
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(5)
<223> OTHER INFORMATION: D-chirality

<400> SEQUENCE: 4

Thr Lys Asn Asp Thr Asn Pro
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 5

Glu Asp Pro Arg Lys Tyr Pro
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (5)..(6)
<223> OTHER INFORMATION: D-chirality

<400> SEQUENCE: 6

Asp Arg Gln Pro Pro Asp Asn
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(5)
<223> OTHER INFORMATION: D-chirality

<400> SEQUENCE: 7

Asp Gln Asn Glu Asn Pro Pro
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (5)..(6)
<223> OTHER INFORMATION: D-chirality

<400> SEQUENCE: 8

Pro Asn Thr Asn Glu Asn Pro
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 9

Gln Ala Pro Asp Asn Asn Asp
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (5)..(6)
<223> OTHER INFORMATION: D-chirality

<400> SEQUENCE: 10

Asn Lys Arg Pro Thr Asp Lys
1               5

<210> SEQ ID NO 11
<211> LENGTH: 7
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 11

Asp Gln Asp Arg Arg Pro Pro
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (6)..(7)
<223> OTHER INFORMATION: D-chirality

<400> SEQUENCE: 12

Lys Tyr Pro Asn Asp Gln Pro Asn
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality

<400> SEQUENCE: 13

Arg Glu Pro Gln Arg Glu Pro Gln
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (8)..(8)
<223> OTHER INFORMATION: D-chirality
```

-continued

```
<400> SEQUENCE: 14

Pro Arg Ala Gln Tyr Pro Asp Glu
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 15

Pro Arg Ala Val His Glu Asp Pro
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (6)..(7)
<223> OTHER INFORMATION: D-chirality

<400> SEQUENCE: 16

Asp Glu Pro Gln Glu Pro Asn Asn
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (7)..(8)
<223> OTHER INFORMATION: D-chirality

<400> SEQUENCE: 17

Pro Ser Gln Pro Arg His Lys His
1               5

<210> SEQ ID NO 18
<211> LENGTH: 8
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (6)..(6)
<223> OTHER INFORMATION: D-chirality

<400> SEQUENCE: 18

Asp Asn Pro Asp Asn Asp Lys Asn
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 19

Tyr Asp Gln Leu Pro Pro Leu Lys
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 20

Asp Glu Pro Asn Gln Lys Asp Asn
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (5)..(6)
<223> OTHER INFORMATION: D-chirality

<400> SEQUENCE: 21
```

Asn Asp Ala Pro Pro Ala Lys His
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 22

Arg Asp Glu Asp Pro Arg Arg Asp
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (4)..(8)
<223> OTHER INFORMATION: D-chirality

<400> SEQUENCE: 23

Glu Tyr Pro Ser Pro Thr Ser Asn
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(6)
<223> OTHER INFORMATION: D-chirality

<400> SEQUENCE: 24

Asn Asn Asp Glu Pro His Arg Lys
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE

```
<222> LOCATION: (7)..(8)
<223> OTHER INFORMATION: D-chirality

<400> SEQUENCE: 25

Pro Lys Thr Glu Pro Ala Thr Asn
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (6)..(8)
<223> OTHER INFORMATION: D-chirality

<400> SEQUENCE: 26

Gln Glu Ala Pro Gln Asp Pro Asn
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (6)..(8)
<223> OTHER INFORMATION: D-chirality

<400> SEQUENCE: 27

Lys Lys Thr Glu Pro Glu Glu Pro
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (7)..(8)
<223> OTHER INFORMATION: D-chirality

<400> SEQUENCE: 28
```

```
Thr Asn Asp Glu Ala Pro Ser Pro
1               5
```

```
<210> SEQ ID NO 29
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (6)..(7)
<223> OTHER INFORMATION: D-chirality

<400> SEQUENCE: 29

Glu Pro Ala Lys Asp Lys His Lys
1               5
```

```
<210> SEQ ID NO 30
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(6)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 30

Lys Val Pro Asp Gln Ile Pro Asn
1               5
```

```
<210> SEQ ID NO 31
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 31

Ser Lys Glu Lys Thr Asp Pro Glu
1               5
```

```
<210> SEQ ID NO 32
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(6)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 32

Asp Asp Pro Thr Pro Arg Gln Gln
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 33

Asp Asn Lys Asp His Pro Asn Asp Lys
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(6)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 34

His Lys Ser Pro Ser Lys Ser Glu Asp
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (7)..(8)
<223> OTHER INFORMATION: D-chirality

<400> SEQUENCE: 35

Ile Pro Pro Val Ile Glu Asn Asp Gln
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 36

Pro Arg Lys Leu Pro Asp Glu Gln Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 37

Pro Ser Asn Glu Arg Asp Asp Thr Gln
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-chirality
<220> FEATURE:
```

```
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 38

Gln Phe Pro Asp Thr Lys Asp Ala Asp
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 39

Arg Ala Pro Pro Lys Pro Asp Lys Asp
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality

<400> SEQUENCE: 40

Val Gln Pro Pro Ala Thr Asp Glu Ser
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
```

```
<221> NAME/KEY: MISC_FEATURE
<222> LOCATION: (6)..(7)
<223> OTHER INFORMATION: D-chirality

<400> SEQUENCE: 41

Pro Ala Glu Pro Asn Thr Lys Ser Pro
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 42

Gln Gln Pro Ile Pro Asp Ala Asp Asp
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 43

Gln His Pro Glu Pro Pro Ser Leu Asp
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (6)..(9)
<223> OTHER INFORMATION: D-chirality

<400> SEQUENCE: 44

His Ala Gln Asp Asn Asp Pro Ser Lys
1               5

<210> SEQ ID NO 45
<211> LENGTH: 9
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 45

Asp Asn Lys Ser Gln Asp Asn Val Asp
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 46

Pro Thr Thr Glu Lys Asp Val Pro Gln
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (6)..(6)
<223> OTHER INFORMATION: D-chirality

<400> SEQUENCE: 47

Pro Asn Asp Ala Pro Pro Glu Pro Leu
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (6)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 48

Pro Pro Thr Ala Pro Pro Asp Asp Lys
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(7)
<223> OTHER INFORMATION: D-chirality

<400> SEQUENCE: 49

Glu Asn Pro Pro Ile Ala Pro Asp Asn
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 50

Pro Asn Asp Ser Asp Lys Pro Asn Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
```

```
<220> FEATURE:
<221> NAME/KEY: MISC_FEATURE
<222> LOCATION: (7)..(8)
<223> OTHER INFORMATION: D-chirality

<400> SEQUENCE: 51

Val Asp Asp His Pro Arg Pro Asn
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 52

Asp Lys Thr Asn Asp Pro Pro Ala Lys
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (4)..(6)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 53

Pro Pro Ser Ser Ser Asn Lys Ser Arg
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (9)..(9)
<223> OTHER INFORMATION: D-chirality
```

```
<400> SEQUENCE: 54

Pro Asn Tyr His Pro Lys Asp Leu Gln
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (5)..(8)
<223> OTHER INFORMATION: D-chirality

<400> SEQUENCE: 55

Thr Gln Asn Asn Asp Pro Arg Ser Ser
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 56

Pro Asn Asp Gln Pro Asn Lys Glu His
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (8)..(8)
<223> OTHER INFORMATION: D-chirality
```

```
<400> SEQUENCE: 57

Pro Pro Asp Asp Lys Pro Asn Lys
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 58

Pro Lys Asp Thr Asp Gln Glu Pro Glu
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 59

Pro Pro Tyr Pro Asp Ser Arg Ile Ala
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 60

Val Leu Asp Asp Ser Val Val Pro Pro
1               5

<210> SEQ ID NO 61
```

```
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 61

Pro Glu Ser Ala Lys Asp Asp Leu Asn
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(5)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 62

Pro Glu Thr Lys Pro Asn Val Val Pro
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 63

Ala Lys His Asn His Asp Lys Asp Asn
1               5

<210> SEQ ID NO 64
```

```
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 64

Lys Gln Asp Pro Arg His Asp Lys Asp
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (6)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 65

Ser Tyr Gln Asp Asn Ala Ile Asn Thr
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(8)
<223> OTHER INFORMATION: D-chirality

<400> SEQUENCE: 66

Gln Pro Asn Val Asp Lys Asp Asn Thr
1               5

<210> SEQ ID NO 67
```

```
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 67

Asp Val Pro Pro Ala Glu Arg Pro Pro
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 68

Pro Asp Asn Val Pro Pro Thr Val Lys
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(9)
<223> OTHER INFORMATION: D-chirality

<400> SEQUENCE: 69

Val Arg Pro Ser Val Gln Glu Pro Asn
```

```
<210> SEQ ID NO 70
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (6)..(8)
<223> OTHER INFORMATION: D-chirality

<400> SEQUENCE: 70

Ala Pro Ser Ala Asp Gln Asn Pro Asn
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 71

Val Pro Asp Arg Val Leu Pro Asn Tyr
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 72

Thr Asp Gln Asp Glu Pro Thr Lys Glu
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (8)..(9)
```

<223> OTHER INFORMATION: D-chirality

<400> SEQUENCE: 73

Asp Pro Asn Lys Asp Asp Arg Thr Tyr
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 74

Pro Asp Asn Ser Pro Thr Gln Gln Tyr
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (5)..(5)
<223> OTHER INFORMATION: D-chirality

<400> SEQUENCE: 75

Ser Pro Ser Asp Gln Asp Ser Ser Ser
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(7)
<223> OTHER INFORMATION: D-chirality

<400> SEQUENCE: 76

Ile Pro Asp Arg Thr Asp Asp Ser Lys
1               5

```
<210> SEQ ID NO 77
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(9)
<223> OTHER INFORMATION: D-chirality

<400> SEQUENCE: 77

Pro Asn Gln Asn Gln Asp Leu Pro Ile
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 78

Asp Glu Pro Asn Gln Pro Asn Asp Asp
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 79

Pro Thr Asp Asp Glu Asn Thr Lys His
1               5
```

```
<210> SEQ ID NO 80
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 80

Glu Lys Asn Ser Asn Glu Lys Pro Pro
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 81

Pro Asp Gln Tyr Arg Asp Pro Tyr Asp
1               5

<210> SEQ ID NO 82
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 82
```

```
Asp Asp Glu Lys Lys Asn Glu Pro Asp Ala
1               5                   10
```

<210> SEQ ID NO 83
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (5)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 83

```
Gln Glu Asp Arg Thr Glu Glu Pro Arg Arg
1               5                   10
```

<210> SEQ ID NO 84
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 84

```
Tyr Pro Ala Gln Pro Pro Leu Leu Lys Asp
1               5                   10
```

<210> SEQ ID NO 85
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 85

```
Asn Lys Glu Lys Asp Lys Ala Pro Glu Pro
1               5                   10
```

```
<210> SEQ ID NO 86
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 86

Glu Pro Asp Lys Pro Asn Ala Asp Gln Gln
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 87

Gln Pro Asn Ala Asp Lys Ala Glu Val Pro
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: D-chirality
<220> FEATURE:
<221> NAME/KEY: MISC_FEATURE
<222> LOCATION: (6)..(7)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 88

Asn Ser Lys Asp Asp Thr Glu Pro Asn Pro
1               5                   10
```

```
<210> SEQ ID NO 89
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(6)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 89

Pro Glu Pro Glu Pro Val Pro Ala Lys Ala
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (7)..(9)
<223> OTHER INFORMATION: D-chirality

<400> SEQUENCE: 90

Pro Arg Ala Lys Leu Pro Asn Ser Asp Ala
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 91

Glu Pro Pro Asn Ala Lys Asp Asn Asn Ala
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
```

```
<222> LOCATION: (4)..(4)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 92

Lys Asp Gln Pro Pro Gln Arg Lys Asp Asn
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (5)..(6)
<223> OTHER INFORMATION: D-chirality
<220> FEATURE:
<221> NAME/KEY: MISC_FEATURE
<222> LOCATION: (8)..(8)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 93

Arg Asp Lys Asp Lys Glu Pro Pro Asp Ala
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 94

Glu Asn Pro Ala Lys Lys Pro Asp His Lys
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
```

```
<222> LOCATION: (6)..(7)
<223> OTHER INFORMATION: D-chirality

<400> SEQUENCE: 95

Lys Asn Pro Pro Thr Glu Pro Ala Ala
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (5)..(6)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 96

Ala Pro Asn Tyr Ser Lys Asp Asn Pro Lys
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (8)..(10)
<223> OTHER INFORMATION: D-chirality

<400> SEQUENCE: 97

Leu Pro Arg Gln Pro Asn Asp Ser Lys Thr
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(6)
<223> OTHER INFORMATION: D-chirality
<220> FEATURE:
<221> NAME/KEY: MISC_FEATURE
<222> LOCATION: (8)..(10)
<223> OTHER INFORMATION: D-chirality

<400> SEQUENCE: 98

Glu Pro Asn Ser Glu Pro Asn Asp Ser Asn
1               5                   10

<210> SEQ ID NO 99
<211> LENGTH: 10
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 99

Lys Asp Asn Asp Pro Asn Asn Lys Leu Asp
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (7)..(8)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 100

Pro Asn Glu Pro Lys Tyr Lys Asn Asp Glu
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 101

Ala Lys Asp Lys Asp Asn Lys Asp Pro Lys
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (9)..(9)
<223> OTHER INFORMATION: D-chirality
```

```
<400> SEQUENCE: 102

Gln Gln Asp Asp Lys Asp Gln Pro Pro Asp
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (8)..(10)
<223> OTHER INFORMATION: D-chirality

<400> SEQUENCE: 103

Glu Glu Pro Lys Ile Pro Asp Lys Glu Ile
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 104

Pro Asp Val Lys Pro Pro Glu Leu Lys Pro
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 105

Glu Glu Ser Pro Ser Ser Pro Asn Thr Asp
1               5                   10
```

<210> SEQ ID NO 106
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 106

Lys Asp Gln Pro Lys Asn Pro Asp Gln Phe
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (5)..(6)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 107

Arg Tyr Ser Trp Arg Asp Pro Tyr Gln Pro
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (5)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 108

Tyr Asp Pro Arg Asp Ser Lys Gln Pro Asn
1               5                   10

<210> SEQ ID NO 109
<211> LENGTH: 10

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (7)..(8)
<223> OTHER INFORMATION: D-chirality

<400> SEQUENCE: 109

Asn Tyr Pro Asp Pro Arg Tyr Pro Asp Pro
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 110

Gln Arg Asn His Pro Asp Thr Gln Pro Asp
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 111

Leu Gln Thr Arg Pro Ser Ala Glu Pro Asp
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (8)..(8)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 112

Gln Tyr Lys His Asp His Pro His Pro Asp
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 113

Ala Asn Asn His Pro Asn Ala Asp Pro Ala
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (5)..(6)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 114

Gln Pro Thr Asn Ile Pro Asn Asp Glu Asp
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Synthetic
```

<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 115

Lys Asp Asn Pro Asn Ala Asp Pro Lys Asp
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(10)
<223> OTHER INFORMATION: D-chirality

<400> SEQUENCE: 116

Pro Arg Asp Gln Glu Pro Asn Ser Ser Asn
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 117

Leu Val Arg Asn His Pro Asp Glu Asn
1               5                   10

<210> SEQ ID NO 118
<211> LENGTH: 10

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 118

Gln Ala Pro Asn Lys Arg Lys Pro Asp Asp
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 119

Ala Pro Ser Ile Gln Pro Asn Glu Asn Asn
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 120

Asn Asn Lys Asp Asn Asp Pro Ala Arg Pro
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
```

```
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (8)..(10)
<223> OTHER INFORMATION: D-chirality

<400> SEQUENCE: 121

Pro Pro Glu Ala Arg Glu Glu Pro Ala Gln
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (5)..(6)
<223> OTHER INFORMATION: D-chirality

<400> SEQUENCE: 122

Tyr Pro His Pro Asn Tyr Glu Asp Lys Asp
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (6)..(6)
<223> OTHER INFORMATION: D-chirality

<400> SEQUENCE: 123

Gln Pro Asp Pro Asn Val Glu Met Lys Asp
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 124

Asp Pro Asn Lys Lys Glu Asp Glu Asn Ser
```

```
<210> SEQ ID NO 125
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(8)
<223> OTHER INFORMATION: D-chirality

<400> SEQUENCE: 125

Asn Ala Gln Asp Asn Pro Glu Pro Lys Pro
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 126

Pro Asp Gln Asp Asp Pro Arg Arg Ser Ala
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 127

His Asn Ser Glu Ala Asn Pro Asn Arg Ala
```

<210> SEQ ID NO 128
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(5)
<223> OTHER INFORMATION: D-chirality
<220> FEATURE:
<221> NAME/KEY: MISC_FEATURE
<222> LOCATION: (7)..(8)
<223> OTHER INFORMATION: D-chirality

<400> SEQUENCE: 128

Asn Asp Gln Lys Asp Asn Ser Glu Pro Pro
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(5)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 129

Glu Tyr Pro Lys Ser Ala Ala Pro Lys Gln
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 130

Pro His Pro Asn Asp Val Asn Asn Asn Arg
1               5                   10

<210> SEQ ID NO 131
<211> LENGTH: 10
<212> TYPE: PRT
<213> ORGANISM: Artificial Sequence
<220> FEATURE:

```
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (5)..(6)
<223> OTHER INFORMATION: D-chirality

<400> SEQUENCE: 131

Tyr Pro Asp Tyr Ile Pro Asp Asp Arg Tyr
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 132

Ser Lys Asp Ala Pro Glu Glu Pro Arg Arg
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (4)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 133

Lys Glu Pro Ser Ser Ala Glu Pro Asn Asp
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (5)..(7)
```

```
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 134

Ser Pro Ala Lys Pro Asn Ser Gln Pro Asn
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(10)
<223> OTHER INFORMATION: D-chirality

<400> SEQUENCE: 135

Asp Asn Lys Asn Pro Pro Asp Gln Ser Gln
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (6)..(7)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 136

Asp Ser Pro Asn Leu Ser Asp Gln Gln Pro
1               5                   10

<210> SEQ ID NO 137
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 137

Asp Ser Pro Asn Leu Asn Lys Asp Val Pro
1               5                   10
```

-continued

```
<210> SEQ ID NO 138
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 138

Thr Glu Pro Gln Ser Glu Pro Pro Asn Leu
1               5                   10

<210> SEQ ID NO 139
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: D-chirality
<220> FEATURE:
<221> NAME/KEY: MISC_FEATURE
<222> LOCATION: (7)..(9)
<223> OTHER INFORMATION: D-chirality

<400> SEQUENCE: 139

Asp Glu Ala Pro Asn Lys Glu Arg Pro Asn
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(10)
<223> OTHER INFORMATION: D-chirality

<400> SEQUENCE: 140

Asn Lys Leu Pro Pro Asp Ala Thr Asn Glu
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (1)..(3)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 141

Arg Lys Glu Pro Ala Glu Asp Asn Pro Asn
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 142

Pro Asn Arg Thr Glu Pro Ala Glu Tyr Asp
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 143

Leu Pro Glu Pro Tyr Ala Leu Lys Pro Asn
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
```

```
<222> LOCATION: (4)..(5)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 144

Lys Ser Pro Pro Asn Asp Asn Lys Asp Val
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (6)..(6)
<223> OTHER INFORMATION: D-chirality

<400> SEQUENCE: 145

Val Pro Asp His Asn Asn Pro Asp His Asn
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (6)..(10)
<223> OTHER INFORMATION: D-chirality

<400> SEQUENCE: 146

Lys Glu Val Pro Asn Thr Ser Pro Ser Ala
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(8)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 147
```

```
Thr Asp Asp Gln Ala Ile Pro Pro Val
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (8)..(8)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 148

Lys Arg Lys Leu Pro Glu Pro Glu Glu Ala
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (4)..(6)
<223> OTHER INFORMATION: D-chirality
<220> FEATURE:
<221> NAME/KEY: MISC_FEATURE
<222> LOCATION: (8)..(8)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 149

Glu Pro Asp Ser Ser Asn Glu Tyr Pro Arg
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (7)..(8)
<223> OTHER INFORMATION: D-chirality

<400> SEQUENCE: 150
```

Asp Lys Lys Leu Ala Pro Asn Asp Pro
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 151

Pro Ala Ser Asp Pro Arg Arg Glu Gln Pro
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (5)..(6)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 152

Glu Ala Lys Asp Val Pro Asp Asn Met Pro
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 153

Met Asn Lys Lys Pro Asp Ala Thr Pro Asp
1               5                   10

```
<210> SEQ ID NO 154
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(8)
<223> OTHER INFORMATION: D-chirality

<400> SEQUENCE: 154

Ala Gln Tyr Pro Asp Gln Arg Gln Pro Ala
 1               5                  10

<210> SEQ ID NO 155
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (6)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 155

Pro His Lys Gln Pro Asp Asp Asn Asn Glu
 1               5                  10

<210> SEQ ID NO 156
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (7)..(8)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 156

Asp Ala Pro Pro Asn Asp Asp Asn Pro Ser
 1               5                  10
```

<210> SEQ ID NO 157
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (6)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 157

Lys Asn Asn Asp Gln Asp Lys Tyr Pro Pro
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (5)..(6)
<223> OTHER INFORMATION: D-chirality
<220> FEATURE:
<221> NAME/KEY: MISC_FEATURE
<222> LOCATION: (8)..(10)
<223> OTHER INFORMATION: D-chirality

<400> SEQUENCE: 158

Asn Val Asn Pro Tyr Pro Asp Ala Pro Pro
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 159

Gln Pro Pro Asn Ala Pro Lys Glu Ser Ser
1               5                   10

```
<210> SEQ ID NO 160
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (5)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 160

Asn Ala Pro Asn Thr Ser Asp Glu Asn Lys
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(7)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 161

Gln Glu Pro Pro Ala Ala Ala Gln Asp Lys
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(5)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 162

Asp Ser Pro Ser Asn Asp Pro Arg His Asp
1               5                   10

<210> SEQ ID NO 163
<211> LENGTH: 10
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 163

Val Asp His Lys Gln Pro Pro Ala Lys Glu
1               5                   10

<210> SEQ ID NO 164
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: D-chirality
<220> FEATURE:
<221> NAME/KEY: MISC_FEATURE
<222> LOCATION: (7)..(8)
<223> OTHER INFORMATION: D-chirality

<400> SEQUENCE: 164

Ser Pro Ser Lys Asp Lys Asp Asn Ala Pro
1               5                   10

<210> SEQ ID NO 165
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (7)..(9)
<223> OTHER INFORMATION: D-chirality

<400> SEQUENCE: 165

Arg Pro Asp Asp Pro Asn Asp Lys Arg Asp
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (6)..(8)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 166

Ala Leu Glu Pro Asn Ser Pro Ser Glu Ser
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(8)
<223> OTHER INFORMATION: D-chirality

<400> SEQUENCE: 167

Ser Asp Gln Tyr Pro Asn Ala Pro Asp Asp
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 168

Glu Ala Arg Asp His Lys Val Pro Pro Ala
1               5                   10

<210> SEQ ID NO 169
<211> LENGTH: 10
<212> TYPE: PRT
<213> ORGANISM: Artificial Sequence
<220> FEATURE:
<223> OTHER INFORMATION: Synthetic
<220> FEATURE:
```

```
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality

<400> SEQUENCE: 169

Gln Asp Asn Lys Asp Gln Asp Asn Pro Asp
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 170

Tyr Pro Glu Ala Lys Asp Asn Asn Lys Asp
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 171

Pro Asp Thr Arg Asp Ala Gln Asp Arg Ile
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 172

Lys Pro Gln Glu Pro Pro Asp Ala Asn Lys
1               5                   10
```

```
<210> SEQ ID NO 173
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (5)..(7)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 173

Asp Val Asp Pro Glu His Pro Asn Ala Lys
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (7)..(8)
<223> OTHER INFORMATION: D-chirality

<400> SEQUENCE: 174

Glu Pro Asn Asp Pro Asn Asn Glu Pro Val
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (8)..(8)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 175

Pro Asn Asp Glu Pro Asp Lys Asp Arg His
1               5                   10
```

```
<210> SEQ ID NO 176
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 176

Ser Glu Pro Gln Gln Ser Glu Pro Ala Tyr
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 177

Pro Ala Asp His Lys Asn Arg Lys Glu Pro
1               5                   10

<210> SEQ ID NO 178
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (6)..(7)
<223> OTHER INFORMATION: D-chirality
```

```
<400> SEQUENCE: 178

Asp Asp Gln Leu Pro Asp Val Pro Asn Ala
1               5                   10

<210> SEQ ID NO 179
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (6)..(7)
<223> OTHER INFORMATION: D-chirality

<400> SEQUENCE: 179

Arg Ser Pro Glu Lys Ser Lys Asp Lys Pro
1               5                   10

<210> SEQ ID NO 180
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 180

Pro Asn Lys Asp Asn Glu Pro Ala Arg Glu
1               5                   10

<210> SEQ ID NO 181
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 181

Pro Asn Lys Asp Gln Pro Ser Ala Asp Glu
1               5                   10

<210> SEQ ID NO 182
<211> LENGTH: 10
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (5)..(6)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 182

Ala Asp Arg Tyr Asp Glu Pro Met Pro Ser
1               5                   10

<210> SEQ ID NO 183
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(5)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 183

Lys Asn Lys Ser Glu Pro Pro Asp Pro Ala
1               5                   10

<210> SEQ ID NO 184
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 184

Asp Glu Arg Pro Pro Lys Ala Lys Asp Lys
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(4)
<223> OTHER INFORMATION: D-chirality
```

```
<220> FEATURE:
<221> NAME/KEY: MISC_FEATURE
<222> LOCATION: (9)..(10)
<223> OTHER INFORMATION: D-chirality

<400> SEQUENCE: 185

Ala Asp Arg Asn Asp Pro Arg Ala Thr Ser
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 186

Gln Ala Pro Glu Pro Pro Glu Ala Lys Asp
1               5                   10

<210> SEQ ID NO 187
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: D-chirality
<220> FEATURE:
<221> NAME/KEY: MISC_FEATURE
<222> LOCATION: (6)..(7)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 187

Asn Tyr Glu Pro His Lys Tyr Asp Leu Pro
1               5                   10

<210> SEQ ID NO 188
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (9)..(10)
<223> OTHER INFORMATION: D-chirality
```

```
<400> SEQUENCE: 188

Thr Pro Lys Thr Asp Lys Asp Arg Asp Pro
1               5                   10

<210> SEQ ID NO 189
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: D-chirality
<220> FEATURE:
<221> NAME/KEY: MISC_FEATURE
<222> LOCATION: (6)..(8)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 189

Ala Asp Pro Ser Lys Glu Leu Pro Asp Asn
1               5                   10

<210> SEQ ID NO 190
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 190

Glu Pro Pro Ala Lys Asp His Asn Asp Arg
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(7)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 191

Asp Ala Pro Lys Pro Ser Gln Gln Asp Asn
```

1               5              10

<210> SEQ ID NO 192
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (8)..(10)
<223> OTHER INFORMATION: D-chirality

<400> SEQUENCE: 192

Gln Asn Glu Asn Ala His Gln Asp Pro Arg
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 193

Asn Lys Gln Pro Asp Asn Thr Asn Asp Pro
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (6)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 194

Pro Asn Ala Asn Gln Arg Pro Pro Asp Gln
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (4)..(6)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 195

Asn Tyr Asn Glu Asn Ala Gln His Pro Pro
1               5                   10

<210> SEQ ID NO 196
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(6)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 196

Pro Val Lys Asp Asp His Pro Asn Asp Glu
1               5                   10

<210> SEQ ID NO 197
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 197

Gln Asn Pro Asn Asn Pro Arg Lys Ala Asp
1               5                   10

<210> SEQ ID NO 198

```
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (7)..(10)
<223> OTHER INFORMATION: D-chirality

<400> SEQUENCE: 198

Asp Lys Asp Tyr Glu Pro Pro Thr Ala His
1               5                   10

<210> SEQ ID NO 199
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 199

Asp Asn Ala Pro Asn Asp Lys Asp Gln Ser
1               5                   10

<210> SEQ ID NO 200
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (5)..(8)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 200

Tyr Glu Tyr Pro Asp Leu Pro Ile Pro Ser
1               5                   10

<210> SEQ ID NO 201
<211> LENGTH: 10
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (6)..(7)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 201

Pro Pro Pro Glu Asn Ser Leu Asp Gln Leu
1               5                   10

<210> SEQ ID NO 202
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (7)..(8)
<223> OTHER INFORMATION: D-chirality

<400> SEQUENCE: 202

Asn Glu Ala Glu Pro Lys Ser Ala Ala Asp
1               5                   10

<210> SEQ ID NO 203
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: D-chirality

<400> SEQUENCE: 203

Glu Pro Lys Tyr Asp Gln Asp Met Arg Arg
1               5                   10

<210> SEQ ID NO 204
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 204

Asp Asp Pro Arg Lys Asp Asp Ala Gln Asp
1               5                   10
```

```
<210> SEQ ID NO 205
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(8)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 205

Glu Thr Lys Ala Pro Thr Glu Glu Pro Lys
1               5                   10

<210> SEQ ID NO 206
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (6)..(6)
<223> OTHER INFORMATION: D-chirality

<400> SEQUENCE: 206

Gln Ala Arg Gln Pro Pro Asp Ala Asn Lys
1               5                   10

<210> SEQ ID NO 207
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(8)
<223> OTHER INFORMATION: D-chirality

<400> SEQUENCE: 207

Glu Pro Asn Val Asn Glu Pro Arg Lys Ala
1               5                   10

<210> SEQ ID NO 208
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (1)..(5)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 208

Ser Glu Pro Asp Asn Lys Ala Lys Pro Asn
1               5                   10

<210> SEQ ID NO 209
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 209

Ala Lys Glu Gln Asp Ala Gln Ala Pro Pro
1               5                   10

<210> SEQ ID NO 210
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (5)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 210

Pro Asn Lys Asp Ser Pro Lys Lys Asp Val
1               5                   10

<210> SEQ ID NO 211
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(4)
<223> OTHER INFORMATION: D-chirality
<220> FEATURE:
<221> NAME/KEY: MISC_FEATURE
```

```
<222> LOCATION: (7)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 211

Ser Asp Ser Gln Lys Pro Pro Lys Leu Asp
1               5                   10

<210> SEQ ID NO 212
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (5)..(6)
<223> OTHER INFORMATION: D-chirality
<220> FEATURE:
<221> NAME/KEY: MISC_FEATURE
<222> LOCATION: (9)..(9)
<223> OTHER INFORMATION: D-chirality

<400> SEQUENCE: 212

Tyr Pro Tyr Pro Asp His Ala Asp Gln Lys
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 213

Val Pro Asn Trp Glu Pro Tyr Gln Asp Lys
1               5                   10

<210> SEQ ID NO 214
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
```

```
<222> LOCATION: (3)..(4)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 214

Lys Asp Ala Pro Pro Ala Lys Asp Arg Asn
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (5)..(6)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 215

Gln Asp Lys Glu Ala Pro Pro Lys Asp Asp
1               5                   10

<210> SEQ ID NO 216
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 216

Ala Gln Glu Pro Ala Gln Asp His Pro Asn
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (2)..(4)
<223> OTHER INFORMATION: D-chirality
<220> FEATURE:
<221> NAME/KEY: MISC_FEATURE
<222> LOCATION: (7)..(10)
<223> OTHER INFORMATION: D-chirality

<400> SEQUENCE: 217

Gln Pro Arg Ala Lys Ala Lys Glu Pro Lys
1               5                   10

<210> SEQ ID NO 218
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(9)
<223> OTHER INFORMATION: D-chirality

<400> SEQUENCE: 218

Asp Asp Arg Lys Pro Glu Pro Lys Pro Asp
1               5                   10

<210> SEQ ID NO 219
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (10)..(10)
<223> OTHER INFORMATION: D-chirality

<400> SEQUENCE: 219

Asp Asp Gln Pro Asp Asp Gln Pro Asp
1               5                   10

<210> SEQ ID NO 220
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
```

```
<222> LOCATION: (1)..(1)
<223> OTHER INFORMATION: D-chirality
<220> FEATURE:
<221> NAME/KEY: MISC_FEATURE
<222> LOCATION: (3)..(5)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 220

Pro Asn Ile Asp Pro Asp Pro Arg Asn Arg
1               5                   10

<210> SEQ ID NO 221
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (5)..(6)
<223> OTHER INFORMATION: D-chirality

<400> SEQUENCE: 221

Gln Asp Lys Glu Pro Asp Pro Asn Ala Asp
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (7)..(9)
<223> OTHER INFORMATION: D-chirality

<400> SEQUENCE: 222

Asp Glu Pro Asn Ala Glu Ser Pro Ser Gln
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: D-chirality
<220> FEATURE:
<221> NAME/KEY: MISC_FEATURE
<222> LOCATION: (5)..(6)
<223> OTHER INFORMATION: D-chirality

<400> SEQUENCE: 223

Lys Glu Lys Asp Lys Pro Asp Pro Arg Gln
1               5                   10
```

<210> SEQ ID NO 224
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (6)..(6)
<223> OTHER INFORMATION: D-chirality
<220> FEATURE:
<221> NAME/KEY: MISC_FEATURE
<222> LOCATION: (8)..(10)
<223> OTHER INFORMATION: D-chirality

<400> SEQUENCE: 224

Pro Asn Asp Ala Pro Asp Lys Asp Asn Gln
1               5                   10

<210> SEQ ID NO 225
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 225

Gln Pro Asn Ala Pro Lys Thr Glu Trp Ala
1               5                   10

<210> SEQ ID NO 226
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (8)..(10)
<223> OTHER INFORMATION: D-chirality

<400> SEQUENCE: 226

Glu Pro Pro Ala Lys Asp Asn Lys Ser Ser
1               5                   10

<210> SEQ ID NO 227
<211> LENGTH: 11
<212> TYPE: PRT
<213> ORGANISM: Artificial Sequence
<220> FEATURE:
<223> OTHER INFORMATION: Synthetic
<220> FEATURE:

```
<221> NAME/KEY: MISC_FEATURE
<222> LOCATION: (1)..(1)
<223> OTHER INFORMATION: D-chirality
<220> FEATURE:
<221> NAME/KEY: MISC_FEATURE
<222> LOCATION: (3)..(5)
<223> OTHER INFORMATION: D-chirality
<220> FEATURE:
<221> NAME/KEY: MISC_FEATURE
<222> LOCATION: (8)..(9)
<223> OTHER INFORMATION: D-chirality
<220> FEATURE:
<221> NAME/KEY: MISC_FEATURE
<222> LOCATION: (11)..(11)
<223> OTHER INFORMATION: D-chirality

<400> SEQUENCE: 227

Ala Gln Pro Cys Lys Asp Ser Tyr Cys Pro Ser
1               5                   10

<210> SEQ ID NO 228
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: D-chirality
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality
<220> FEATURE:
<221> NAME/KEY: MISC_FEATURE
<222> LOCATION: (9)..(9)
<223> OTHER INFORMATION: D-chirality
<220> FEATURE:
<221> NAME/KEY: MISC_FEATURE
<222> LOCATION: (12)..(12)
<223> OTHER INFORMATION: D-chirality

<400> SEQUENCE: 228

His Pro Val Cys Leu Pro Pro Glu Lys Val Cys Glu
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: D-chirality
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (10)..(11)
<223> OTHER INFORMATION: D-chirality
<220> FEATURE:
<221> NAME/KEY: MISC_FEATURE
<222> LOCATION: (14)..(14)
<223> OTHER INFORMATION: D-chirality

<400> SEQUENCE: 229
```

```
Pro Cys Asn Val Pro Asp Val Tyr Cys Pro Asn Lys Tyr Val
1               5                  10
```

<210> SEQ ID NO 230
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: D-chirality
<220> FEATURE:
<221> NAME/KEY: MISC_FEATURE
<222> LOCATION: (6)..(6)
<223> OTHER INFORMATION: D-chirality

<400> SEQUENCE: 230

```
Asp Thr Asn Pro Thr Lys Asn
1               5
```

<210> SEQ ID NO 231
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: D-chirality
<220> FEATURE:
<221> NAME/KEY: MISC_FEATURE
<222> LOCATION: (7)..(7)
<223> OTHER INFORMATION: D-chirality

<400> SEQUENCE: 231

```
Asp Gln Ser Glu Pro His Pro
1               5
```

<210> SEQ ID NO 232
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-chirality
<220> FEATURE:
<221> NAME/KEY: MISC_FEATURE
<222> LOCATION: (6)..(7)
<223> OTHER INFORMATION: D-chirality

<400> SEQUENCE: 232

```
Gln Asp Pro Pro Lys Thr Asp
1               5
```

<210> SEQ ID NO 233
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: D-chirality
<220> FEATURE:

```
<221> NAME/KEY: MISC_FEATURE
<222> LOCATION: (3)..(3)
<223> OTHER INFORMATION: D-chirality

<400> SEQUENCE: 233

Lys Tyr Pro Glu Asp Glu Arg
1               5

<210> SEQ ID NO 234
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: D-chirality
<220> FEATURE:
<221> NAME/KEY: MISC_FEATURE
<222> LOCATION: (5)..(6)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 234

Pro Gln Arg Gln Pro Gln Arg Glu
1               5

<210> SEQ ID NO 235
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(5)
<223> OTHER INFORMATION: D-chirality
<220> FEATURE:
<221> NAME/KEY: MISC_FEATURE
<222> LOCATION: (8)..(8)
<223> OTHER INFORMATION: D-chirality

<400> SEQUENCE: 235

Lys Asp Leu Gln Pro Pro Tyr His Pro
1               5

<210> SEQ ID NO 236
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(7)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 236

Pro Glu Ala Ala Arg Val Pro Arg Leu Thr
1               5                   10

<210> SEQ ID NO 237
<211> LENGTH: 10
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: D-chirality
<220> FEATURE:
<221> NAME/KEY: MISC_FEATURE
<222> LOCATION: (5)..(7)
<223> OTHER INFORMATION: D-chirality
<220> FEATURE:
<221> NAME/KEY: MISC_FEATURE
<222> LOCATION: (9)..(10)
<223> OTHER INFORMATION: D-chirality

<400> SEQUENCE: 237

Glu Val Asp Pro Glu His Pro Asn Ala Pro
1               5                   10
```